(12) United States Patent
Kim et al.

(10) Patent No.: US 11,531,023 B2
(45) Date of Patent: Dec. 20, 2022

(54) BIOMARKER FOR DIAGNOSING OVERACTIVE BLADDER DISEASE AND SCREENING METHOD OF THERAPEUTIC AGENTS USING THE SAME

(71) Applicant: Korea Basic Science Institute, Daejeon (KR)

(72) Inventors: Gun H. Kim, Daejeon (KR); Edmond C. Park, Sejong-Si (KR); Seung I. Kim, Daejeon (KR); Sang-Yeop Lee, Daejeon (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 154 days.

(21) Appl. No.: 16/169,020

(22) Filed: Oct. 24, 2018

(65) Prior Publication Data
US 2019/0324015 A1    Oct. 24, 2019

(30) Foreign Application Priority Data

Apr. 19, 2018 (KR) .................. 10-2018-0045813

(51) Int. Cl.
| | | |
|---|---|---|
| *C12Q 1/68* | (2018.01) | |
| *G01N 33/50* | (2006.01) | |
| *G01N 33/53* | (2006.01) | |
| *A61K 31/7088* | (2006.01) | |
| *C07K 16/18* | (2006.01) | |
| *G16H 50/20* | (2018.01) | |
| *G16B 20/00* | (2019.01) | |
| *G16B 40/00* | (2019.01) | |

(52) U.S. Cl.
CPC ..... *G01N 33/5023* (2013.01); *A61K 31/7088* (2013.01); *C07K 16/18* (2013.01); *G01N 33/5308* (2013.01); *G16B 20/00* (2019.02); *G16B 40/00* (2019.02); *G16H 50/20* (2018.01); *G01N 2500/10* (2013.01); *G01N 2800/34* (2013.01); *G01N 2800/60* (2013.01)

(58) Field of Classification Search
None
See application file for complete search history.

(56) References Cited

U.S. PATENT DOCUMENTS

| | | | | |
|---|---|---|---|---|
| 8,187,810 | B2 * | 5/2012 | Bluth ................. | G01N 33/6893 435/6.11 |
| 2006/0258574 | A1 * | 11/2006 | Bodary ................. | A61P 43/00 424/139.1 |

OTHER PUBLICATIONS

Park et al (Molecular Cellular Proteomics, Feb. 2018, vol. 17, pp. 948-960).*
Hesch (Baylor University Medical Center Proceedings, 2007, vol. 20, No. 3, pp. 307-314).*
Park et al., "Proteomic analysis of urothelium of rats with detrusor overactivity induced by bladder outlet obstruction", Molecular & Cellular Proteomics, Manuscript RA117.000290 (Feb. 1, 2018) (35 pgs).

* cited by examiner

*Primary Examiner* — Celine X Qian
(74) *Attorney, Agent, or Firm* — Carter, DeLuca & Farrell LLP; George Likourezos

(57) ABSTRACT

The present invention relates to a biomarker for diagnosis of overactive bladder (OAB) disease, and a method for screening a drug using the biomarker. The markers described in the present invention can effectively detect or diagnose the onset of OAB by distinguishing them from normal populations. In particular, OAB-specific protein markers released into urine enable simple and rapid OAB diagnosis in a non-invasive manner. In addition, by selecting an agent that changes, particularly normalizes the expression and activity of the markers selected in the present invention, more effective preventative or therapeutic agents of OAB disease can be screened.

6 Claims, 8 Drawing Sheets
(6 of 8 Drawing Sheet(s) Filed in Color)

BIOMARKER FOR DIAGNOSING OVERACTIVE BLADDER DISEASE AND SCREENING METHOD OF THERAPEUTIC AGENTS USING THE SAME

CROSS-REFERENCE TO RELATED APPLICATIONS

The present application claims the benefit of priority to Korean Patent Application No. 10-2018-0045813, filed on Apr. 19, 2018, the contents of which are incorporated by reference herein in their entirety.

BACKGROUND

Field

The present invention relates to biomarkers for diagnosing overactive bladder (OAB) disease and a screening method of therapeutic agents using the same. More particularly, the present invention relates to a use for diagnosing OAB disease in agents for measuring activity or expression level and a method of providing information necessary for the diagnosis of OAB disease using thereof. In addition, the present invention relates to a drug screening method for the prevention or treatment of OAB disease comprising selection of agents exhibiting an effect of inhibiting or activating the activity or expression level of at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2, PF4, RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC.

Discussion of the Background

Overactive bladder (OAB) refers to diseases associated with multiple symptoms including urinary urgency, urges incontinence, nocturia, and frequent urination, and has a negative impact on health-related quality of life. A study of 16,776 Europeans reported that the overall prevalence of OAB was 16.6% (Milsom, I. et al. (2001)). In a survey of 5,204 Americans, the prevalence of OAB was reported to be 16.0% for males and 16.9% for females (Stewart, W. F. et al. (2003)). Traditionally, OAB was thought to affect mainly women, but based on the prevalence of patients with lower urinary tract symptoms (LUTS), OAB has been shown to affect men as well. Most bladder outlet obstruction caused by benign prostate hyperplasia can induce hyperactivity of detrusor muscle and is the most common cause of OAB in elderly men. In addition to the physical aspects of this disease, OAB can often have a negative impact on the quality of life as a painful or very common condition. The disease can also lead to serious financial burdens on society through the loss of productivity as well as medical.

The bladder consists of three distinct tissue layers. The innermost layer of the bladder is the mucosal layer surrounding the hollow lumen. Unlike the mucous membranes of other hollow organs, the bladder is surrounded by transitional epithelial tissue called urothelium. Urothelium can expand considerably to contain large volumes of urine and protects tissues below urothelium for acidic or alkaline urine. The middle layer is ubmucosa tissue, which forms a connective tissue layer together with blood vessels and nerve tissue, and supports and regulates the surrounding tissue layers. The outermost layer is a muscular membrane that surrounds the submucosal layer and allows the bladder to expand and contract. Muscle membrane layers are often referred to as detrusor muscle, which causes contractions during urination to release urine from the body.

Although the exact pathogenic mechanism mediating OAB has not been fully understood, it is believed that contributions from neurogenic and myogenic sources are currently available. OAB is generally believed to be associated with changes or dysfunctions of muscarinic receptors in detrusor muscles (Michel, M. C. & Igawa, Y, (2015)). These changes may lead to unstable bladder contractions or excessive activity of detrusor muscle. Thus, the major mechanism of anticholinergic drugs widely used for the treatment of OAB is antagonism to the acetylcholine (Ach) effect on muscarinic receptors in cholinergically stimulated bladder detrusor muscle (Giarenis, I et al., (2015)).

The urothelium of the bladder is known to act mainly as a barrier. However, according to recent studies, urothelium is a responsive structure which is able to sense physiological and chemical stimuli and release various signal molecules and various trophic factors in response to physical or chemical stimuli. The urothelium can act as a sensor and transducer, allowing intercommunication between the urothelium and other bladder tissue layers. Thus, the function of urothelium is closely related to the function of the nervous system, and regulation of signaling pathway activity in urothelium may be a new therapeutic strategy for the treatment of OAB. However, existing OAB studies have focused only on bladder detrusor muscle or neural tissue, and detailed analysis of urothelium at the molecular level has not been reported so far.

PRIOR ART DOCUMENT

Non-Patent Document (Non-Patent Document 1) Milsom, I. et al. How widespread are the symptoms of an overactive bladder and how are they managed? A population-based prevalence study. BJU Int 87, 760-766 (2001).
(Non-Patent Document 2) Stewart, W. F. et al. Prevalence and burden of overactive bladder in the United States., World J Urol 20, 327-336 (2003).
(Non-Patent Document 3) Michel, M. C. & Igawa, Y. Therapeutic targets for overactive bladder other than smooth muscle. *Expert Opin Ther Targets* 19, 687-705 (2015).
(Non-Patent Document 4) Giarenis, I., Robinson, D. & Cardozo, L. Overactive Bladder and the beta3-Adrenoceptor Agonists: Current Strategy and Future Prospects. Drugs 75, 1707-1713 (2015).
(Non-Patent Document 5) Lluel, P., Duquenne, C. & Martin, D. Experimental bladder instability following bladder outlet obstruction in the female rat. J Urol 160, 2253-2257 (1998).
(Non-Patent Document 6) Lee, T., Andersson, K. E., Streng, T. & Hedlund, P. Simultaneous registration of intraabdominal and intravesical pressures during cystometry in conscious rats-effects of bladder outlet obstruction and intravesical PGE2. *Neurourol Urodyn* 27, 88-95 (2008).
(Non-Patent Document 7) Park, E. C. et al. Analysis of the endoplasmic reticulum subproteome in the livers of type 2 diabetic mice. Int J Mol Sci 13, 17230-17243 (2012).

Therefore, while the inventors of the present invention have been studying to develop OAB diagnostic markers at the molecular level in order to solve the problem that the clinical diagnosis of OAB is based on symptom, the inventors of the present invention have completed the present invention after they have identified that the marker proteins of the urothelium are associated with OAB disease and in particularly, confirmed that OAB can be diagnosed non-invasively through OAB-specific protein markers released into urine, as well as confirmed that it is possible to screen for therapeutic agents for prevention or treatment of OAB disease more effectively by selecting therapeutic agents that change (especially, normalize) the expression (and activity) pattern of the markers

SUMMARY

Exemplary embodiments provide a method for diagnosing and treating overactive bladder disease in a subject, the method comprising:

(a) obtaining a biological sample from a suspected subject of overactive bladder disease, (b) measuring the activity or the expression level of at least one selected from the group consisting of Anxa5 (Annexin A5), Slc12a7(solute carrier family 12 member 7), Vamp8(Vesicle-associated membrane protein 8), Cacna2d1 (Voltage-dependent calcium channel subunit alpha-2/delta-1), Lgals3 bp(galectin 3 binding protein), Pgrmc1(Membrane-associated progesterone receptor component 1), ENTPD1(Ectonucleoside Triphosphate Diphosphohydrolase 1), P2RX1(P2X purinoceptor 1), ATP5B(ATP synthase subunit beta), VAMP2(Vesicle-associated membrane protein 2), EIF4B(Eukaryotic translation initiation factor 4B), PTMA(Prothymosin Alpha), C2(complement component 2), C3(complement component 3), C4A(complement component 4A), C4B(complement component 4B), CFH(complement factor H), CILP(cartilage intermediate layer protein), IGFBP7(insulin-like growth factor binding protein 7), ITIH1(inter-alpha-trypsin inhibitor heavy chain 1), MGP (matrixGla protein), NID2(nidogen 2), PF4(platelet factor 4), RBP4(Retinol binding protein 4), RPSA(40S ribosomal protein SA), PIN2(Auxin efflux carrier component 2), CP(ceruloplasmin), SOD2(superoxide dismutase 2), HSPD1 (60 kDa heat shock protein family D member 1), PEF1 (Peflin), 1300017J02Rik protein, A1BG(alpha-1-B glycoprotein), CFL2(cofilin 2), CPA3(carboxypeptidase A3), ECM1(extracellular matrix protein 1), FBLN5(fibulin 5), FGB(fibrinogen beta chain), FMOD(fibromodulin), GPX3 (glutathione peroxidase 3), HBA1(hemoglobin alpha 1), HBA2(hemoglobin alpha 2), HP(haptoglobin), ITIH4(inter-alpha-trypsin inhibitor heavy chain family member 4), LAMC1(laminin gamma 1), LTBP4(latent transforming growth factor beta binding protein 4), PCOLCE(procollagen C-endopeptidase enhancer), PRG2(proteoglycan 2), PXDN (peroxidasin), SERPINA6(serpin peptidase inhibitor clade A member 6), SUSD2(sushi domain containing 2), TINAGL1(tubulointerstitial nephritis antigen-like 1) and TNC(tenascin C) in the biological sample;

(c) diagnosing the subject with overactive bladder disease when (i) the expression or detection level of at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2 and PF4 from the biological sample is greater than that of a normal control sample, and (ii) the expression or detection level of at least one selected from the group consisting of RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC from the biological sample is smaller than that of a normal control sample; and (d) treating the diagnosed subject by administering an effective amount of a therapeutic agent for overactive bladder disease.

An exemplary embodiment discloses the above diagnosis and treatment method wherein the protein is selected from the group consisting of C2, C3, C4A, C4B, CFH, CILP, IGFBP7, ITIH1, MGP, NID2, PF4, 1300017J02Rik protein, A1BG, CFL2, CP, CPA3, ECM1, FBLN5, FGB, FMOD, GPX3, HBA1, HBA2, HP, ITIH4, LAMC1, LTBP4, PCOLCE, PRG2, PXDN, RBP4, SERPINA6, SUSD2, TINAGL1 and TNC.

Still another exemplary embodiment discloses the method wherein step (b) is conducted by an agent comprising (I) an antibody which specifically binds to the protein of claim 1, a peptide or aptamer having a binding domain specific to the protein; or (II) a primer or a probe which specifically binds to mRNA of a gene encoding the protein of claim 1.

Still another exemplary embodiment discloses the method wherein the probe is at least one selected from the group consisting of an oligonucleotide probe, a single stranded DNA probe, a double stranded DNA probe and a RNA probe.

Still further exemplary embodiment discloses the method wherein step (c) is conducted by a kit comprising an agent for measuring the activity or the expression level of at least one selected from the group consisting of Anxa5(Annexin A5), Slc12a7(solute carrier family 12 member 7), Vamp8 (Vesicle-associated membrane protein 8), Cacna2d1(Voltage-dependent calcium channel subunit alpha-2/delta-1), Lgals3 bp(galectin 3 binding protein), Pgrmc1(Membrane-associated progesterone receptor component 1), ENTPD1 (Ectonucleoside Triphosphate Diphosphohydrolase 1), P2RX1(P2X purinoceptor 1), ATP5B(ATP synthase subunit beta), VAMP2(Vesicle-associated membrane protein 2), EIF4B(Eukaryotic translation initiation factor 4B), PTMA (Prothymosin Alpha), C2(complement component 2), C3(complement component 3), C4A(complement component 4A), C4B(complement component 4B), CFH(complement factor H), CILP(cartilage intermediate layer protein), IGFBP7(insulin-like growth factor binding protein 7), ITIH1(inter-alpha-trypsin inhibitor heavy chain 1), MGP (matrixGla protein), NID2(nidogen 2), PF4(platelet factor 4), RBP4(Retinol binding protein 4), RPSA(40S ribosomal protein SA), PIN2(Auxin efflux carrier component 2), CP(ceruloplasmin), SOD2(superoxide dismutase 2), HSPD1 (60 kDa heat shock protein family D member 1), PEF1 (Peflin), 1300017J02Rik protein, A1BG(alpha-1-B glycoprotein), CFL2(cofilin 2), CPA3(carboxypeptidase A3), ECM1(extracellular matrix protein 1), FBLN5(fibulin 5), FGB(fibrinogen beta chain), FMOD(fibromodulin), GPX3 (glutathione peroxidase 3), HBA1(hemoglobin alpha 1), HBA2(hemoglobin alpha 2), HP(haptoglobin), ITIH4(inter-alpha-trypsin inhibitor heavy chain family member 4), LAMC1(laminin gamma 1), LTBP4(latent transforming growth factor beta binding protein 4), PCOLCE(procollagen C-endopeptidase enhancer), PRG2(proteoglycan 2), PXDN (peroxidasin), SERPINA6(serpin peptidase inhibitor clade A member 6), SUSD2(sushi domain containing 2), TINAGL1(tubulointerstitial nephritis antigen-like 1) and TNC(tenascin C) in the biological sample.

Another exemplary embodiment discloses a method for detecting an amount of at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2, PF4, RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC in a sample of a subject, the method comprising:

(a) obtaining a biological sample from a suspected subject of overactive bladder disease; and (b) detecting an amount of at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2, PF4, RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC in the biological sample.

Still another exemplary embodiment discloses a method for screening an agent for the prevention or treatment of overactive bladder disease, the method comprising:

(a) culturing a cell expressing at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2 and PF4 with or without a test agent; and (b) comparing the degree of expression or activity of the protein of step (a) in between the cell cultured with the test agent and the cell cultured without the test agent, and thereby confirming whether the test agent inhibits the expression or activity of the protein of step (a).

Still another exemplary embodiment discloses a method for screening an agent for the prevention or treatment of overactive bladder disease, the method comprising:

(a) culturing a cell expressing at least one selected from the group consisting of RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC with or without a test agent; and (b) comparing the degree of expression or activity of the protein of step (a) in between the cell cultured with the test agent and the cell cultured without the test agent, and thereby confirming whether the test agent increases the expression or activity of the protein of step (a).

Additional aspects will be set forth in the detailed description which follows, and, in part, will be apparent from the disclosure, or may be learned by practice of the inventive concept.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows regular urination patterns, stable basal pressure (BP) and threshold pressure (TP) as a sham-operated group. FIG. 1B shows unstable BP, obscure TP, short micturition interval (MI) and increased slope as OAB rat groups prepared through partial bladder outlet obstruction. The intermicturition pressure (IMV) was expressed in cmH$_2$O and micturition volume (MV) was expressed in ml.

FIG. 3A shows the results of classifying the subcellular localization of proteins found in the urothelium of sham rat. FIG. 3B shows the results of classifying the subcellular localization of proteins found in the urothelium of OAB rat. The numbers in the graph indicate the number of proteins.

DETAILED DESCRIPTION OF THE ILLUSTRATED EMBODIMENTS

Figure 1A:
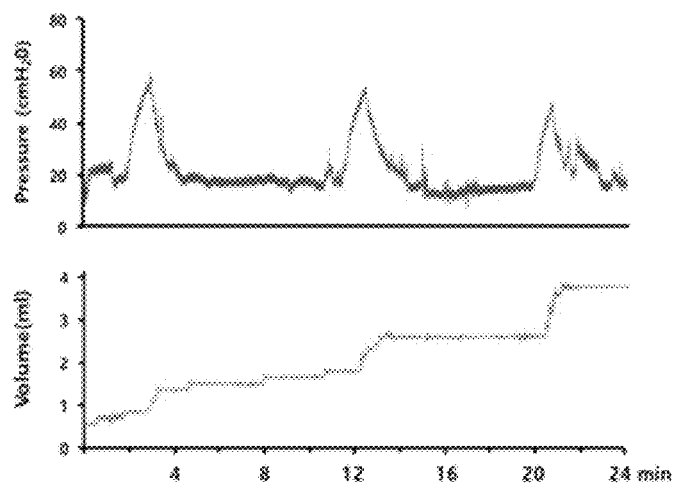
FIG. 1A and FIG. 1B show a follow-up result of a representative pressure inside of the bladder.

Hereinafter, the present invention will be described in detail.

The inventors of the present invention have identified 355 marker genes (and/or proteins expressed therefrom) that are differentially expressed in overactive bladder (OAB) disease. Of these, the below-mentioned 52 marker proteins and the genes encoding them are particularly valuable as diagnostic markers for overactive bladder (OAB) disease.

Accordingly, the present invention provides a composition for the diagnosis of overactive bladder disease, the composition comprising, as an active ingredient, at least one selected from the group consisting of Anxa5(Annexin A5), Slc12a7(solute carrier family 12 member 7), Vamp8 (Vesicle-associated membrane protein 8), Cacna2d1(Voltage-dependent calcium channel subunit alpha-2/delta-1), Lgals3 bp(galectin 3 binding protein), Pgrmc1(Membrane-associated progesterone receptor component 1), ENTPD1 (Ectonucleoside Triphosphate Diphosphohydrolase 1), P2RX1(P2X purinoceptor 1), ATP5B(ATP synthase subunit beta), VAMP2(Vesicle-associated membrane protein 2), EIF4B(Eukaryotic translation initiation factor 4B), PTMA (Prothymosin Alpha), C2(complement component 2), C3(complement component 3), C4A(complement component 4A), C4B(complement component 4B), CFH(complement factor H), CILP(cartilage intermediate layer protein), IGFBP7(insulin-like growth factor binding protein 7), ITIH1(inter-alpha-trypsin inhibitor heavy chain 1), MGP (matrixGla protein), NID2(nidogen 2), PF4(platelet factor 4), RBP4(Retinol binding protein 4), RPSA(40S ribosomal protein SA), PIN2(Auxin efflux carrier component 2), CP(ceruloplasmin), SOD2(superoxide dismutase 2), HSPD1 (60 kDa heat shock protein family D member 1), PEF1 (Peflin), 1300017J02Rik protein, A1BG(alpha-1-B glycoprotein), CFL2(cofilin 2), CPA3(carboxypeptidase A3), ECM1(extracellular matrix protein 1), FBLN5(fibulin 5), FGB(fibrinogen beta chain), FMOD(fibromodulin), GPX3 (glutathione peroxidase 3), HBA1(hemoglobin alpha 1), HBA2(hemoglobin alpha 2), HP(haptoglobin), ITIH4(inter-alpha-trypsin inhibitor heavy chain family member 4), LAMC1(laminin gamma 1), LTBP4(latent transforming growth factor beta binding protein 4), PCOLCE(procollagen C-endopeptidase enhancer), PRG2(proteoglycan 2), PXDN (peroxidasin), SERPINA6(serpin peptidase inhibitor clade A member 6), SUSD2(sushi domain containing 2), TINAGL1(tubulointerstitial nephritis antigen-like 1) and TNC(tenascin C), and a kit comprising the same.

Specifically, the present invention is to provide a composition for the diagnosis of overactive bladder disease, the composition comprising an agent for measuring the activity or expression level of at least one selected from the group, and a kit comprising the same.

The overactive bladder (OAB) disease is a complication accompanied by complex symptoms such as urinary urgency, urge incontinence, nocturia, and frequent urination. The OAB means a phenomenon that the bladder sensory nerve is so sensitive that while it stores urine in the bladder, regardless of the person's intention, the bladder muscle contracts, feels a sudden urination and urinates frequently. According to the definition of the International Incontinence Institute, the OAB disease refers to, regardless of the person's intention to suppress, the case of involuntary detrusor contraction in the bladder filling period. It means to have the symptoms of almost urinary frequency and nocturia with the urinary urgency as dysuria and at this time, urge incontinence may be accompanied or not. In other words, it is known that the OAB disease can be defined if it is accompanied by urinary frequency and urinary urgency regardless of the presence or absence of urge incontinence. Therefore, preferably, the present invention may refer to the OAB disease including (or having) dysuria symptoms selected from the group consisting of urinary frequency, nocturia, and urinary urgency regardless of urge incontinence.

The urge incontinence refers to the symptom of sudden urination and urinary leakage. Urinary frequency (weekly urinary frequency) is a symptom of frequent urination. It is a symptom that urinary frequency is over 8 times a week. The urinary urgency means a symptom that cannot be tolerated when urinating. The nocturia is a symptom that occurs frequently due to urination at night, and is characterized in that it occurs two or more times during urination during bedtime.

In the present invention, the overactive bladder disease may be more preferably overactive bladder symptom related with a bladder outlet obstruction, and the bladder outlet obstruction may be caused by various causes such as stones, benign prostatic hyperplasia, uterine prolapse, constipation, and infection, but is not limited thereto. The present invention includes the overactive bladder disease associated with bladder outlet obstruction due to the various causes described above.

The term "expression" in the present invention means the generation (including increased production) of the desired protein itself or a polynucleotide (particularly, mRNA) encoding the protein, wherein it includes both transcription and translation of a particular nucleic acid sequence triggered by the promoter.

The term "protein" in the present invention is used interchangeably with "a polypeptide" or "peptide". For example, it is a polymer of amino acid residues as commonly found in proteins in nature. In the present invention, the protein is preferably derived from a mammal, more preferably a human.

In the present invention, the term "polynucleotide" or "nucleic acid" refers to deoxyribonucleotide (DNA) or ribonucleotide (RNA) in the form of single- or double-stranded, and especially in DNA, it can be called a gene. Unless otherwise limited, it also includes known analogs of natural nucleotides that hybridize to nucleic acids in a manner similar to naturally occurring nucleotides. In the above RNA, it is understood in the present invention that mRNA is preferably referred to, but is not limited thereto. The term "messenger RNA (mRNA)" is an RNA that specifies an amino acid sequence from a specific gene in the course of protein synthesis, and is an RNA that transfers genetic information (gene-specific base sequence) to a ribosome. In the present invention, the polynucleotide preferably refers to a protein based on a mammalian protein, and more preferably, it may be based on a human protein.

The term "diagnosis" in the present invention is a concept including both determination of susceptibility of an object to a specific disease and confirmation of existence or characteristics of a specific pathological condition for an individual. In the present invention, the diagnosis is to confirm the onset or the possibility (risk) of developing overactive bladder (OAB) disease.

The 52 marker proteins or the genes encoding the proteins (nucleic acids) of the present invention are analyzed in terms of its activity level (amount) or expression level (amount) from a specimen or a biological specimen isolated from suspected individuals. In the present invention, "sample" or "biological sample" includes samples of solid tissues such as blood or other liquid samples of biological origin, biopsy specimens, tissue culture, or cells derived therefrom. More specifically, it may be tissues, cells, cell lysates, whole bloods, plasma, serum, saliva, ophthalmic solution, cerebrospinal fluid, sweat, urine, milk, ascitic fluid synovial fluid, and peritoneal fluid, but is not limited to. In the present invention, the biological sample may be preferably bladder urothelium or urine sample. The urothelium is not limited thereto, but may be preferably mucosal layers of the bladder.

The sample can be obtained from an animal, preferably a mammal, and most preferably from a human. The sample may be pretreated prior to use for detection or diagnosis. For example, it may include homogenization, filtration, distillation, extraction, concentration, inactivation of interfering components, and addition of reagents.

In the present invention, the term "marker" or "biomarker" refers to a substance capable of detecting or diagnosing by distinguishing a tissue, an organ or an individual having overactive bladder disease from a normal tissue, organ or individual. Thus, it includes organic biomolecules such as proteins or nucleic acids (e.g., mRNA), lipids, glycolipids, glycoproteins or sugars (monosaccharides, disaccharides, oligosaccharides, etc.) that show an increase or decrease in the tissues or regions where diseases occur, compared to normal specimens.

In the present invention, it is characterized in that least one protein selected from the group consisting of proteins consisting of Anxa5(Annexin A5), Slc12a7(solute carrier family 12 member 7), Vamp8(Vesicle-associated membrane protein 8), Cacna2d1(Voltage-dependent calcium channel subunit alpha-2/delta-1), Lgals3 bp(galectin 3 binding protein), Pgrmc1(Membrane-associated progesterone receptor component 1), ENTPD1(Ectonucleoside Triphosphate Diphosphohydrolase 1), P2RX1(P2X purinoceptor 1), ATP5B(ATP synthase subunit beta), VAMP2(Vesicle-associated membrane protein 2), EIF4B(Eukaryotic translation initiation factor 4B), PTMA(Prothymosin Alpha), C2(complement component 2), C3(complement component 3), C4A(complement component 4A), C4B(complement component 4B), CFH(complement factor H), CILP(cartilage intermediate layer protein), IGFBP7(insulin-like growth factor binding protein 7), ITIH1(inter-alpha-trypsin inhibitor heavy chain 1), MGP(matrixGla protein), NID2(nidogen 2), PF4(platelet factor 4), RBP4(Retinol binding protein 4), RPSA(40S ribosomal protein SA), PIN2(Auxin efflux carrier component 2), CP(ceruloplasmin), SOD2(superoxide dismutase 2), HSPD1(60 kDa heat shock protein family D member 1), PEF1(Peflin), 1300017J02Rik protein, A1BG (alpha-1-B glycoprotein), CFL2(cofilin 2), CPA3(carboxypeptidase A3), ECM1(extracellular matrix protein 1), FBLN5(fibulin 5), FGB(fibrinogen beta chain), FMOD(fibromodulin), GPX3(glutathione peroxidase 3), HBA1(hemoglobin alpha 1), HBA2(hemoglobin alpha 2), HP(haptoglobin), ITIH4(inter-alpha-trypsin inhibitor heavy chain family member 4), LAMC1(laminin gamma 1), LTBP4 (latent transforming growth factor beta binding protein 4), PCOLCE(procollagen C-endopeptidase enhancer), PRG2 (proteoglycan 2), PXDN(peroxidasin), SERPINA6(serpin peptidase inhibitor clade A member 6), SUSD2(sushi domain containing 2), TINAGL1(tubulointerstitial nephritis antigen-like 1) and TNC(tenascin C) of which expression is increased or decreased in the urothelium and/or the urine of the individuals having the overactive bladder disease in contrast to the normal individuals, respectively; or at least one selected from a group consisting of a gene or polynucleotide encoding the protein group are used as markers.

The specific sequence (amino acid sequence and nucleotide sequence) of each marker protein and the gene encoding it is known through a gene database well known in the art such as Uniprot and Genbank. Those skilled in the art can appropriately select and use sequence information interspersed in the database to construct (make) a specific sequence of each marker and detection or measurement tools based thereon (e.g., antibody, aptamer, primer, probe, etc.).

Specifically, in the Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2 or PF4, its expression level (amount) or detection level (amount) is proportional to the risk of overactive bladder (OAB) disease, whereby expression is increased in a subject having OAB disease. That is, when overexpressing these 23 marker proteins or genes encoding for the above-mentioned proteins, it can be determined that the OAB disease is caused or has a high possibility of developing.

In particular, in the case of the marker proteins of ENTPD1, VAMP2, EIF4B, PTMA, C2, C3, C4A, C4B, CFH, CILP, IGFBP7, ITIH1, MGP, NID2 or PF4, the present inventors discovered for the first time that they are specifically existed or detected only in urothelium and/or urine in the OAB. Therefore, these proteins have an effect capable of determining or diagnosing OAB only by the presence or absence of their expression or the presence or absence of their detection without comparison (or contrast) with the level of expression in normal urothelium and/or urine, and they have great technical value as markers.

In the above RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 or TNC, it is characterized in that its expression level (amount) or detection level (amount) is inversely proportional to the risk of overactive bladder disease, and its expression is reduced in subjects with OAB disease. That is, when these 29 marker proteins or the genes encoding the proteins are low expressed, it can be determined that the OAB disease is caused or has a high possibility of developing.

In particular, in the case of the 29 kinds of marker proteins, the present inventors firstly discovered that they are specifically existed or detected only in normal urothelium and/or urine without being detected in the urothelium and/or urine of OAB. Therefore, these proteins have an effect (or an effect capable of determining or diagnosing normal individuals by distinguishing from the OAB) capable of determining or diagnosing OAB only by the presence or absence of their expression or the presence or absence of their detection without comparison (or contrast) with the level of expression in normal urothelium and/or urine and they have great technical value as markers.

Preferably, among the above-mentioned 52 marker proteins whose expression is differentially changed in the urothelium of the OAB subjects, especially, the markers of the present invention may be preferable to use proteins secreted into urine as markers. Specifically one or more (proteins) selected from the group consisting of C2, C3, C4A, C4B, CFH, CILP, IGFBP7, ITIH1, MGP, NID2, PF4, 1300017J02Rik protein, A1BG, CFL2, CP, CPA3, ECM1, FBLN5, FGB, FMOD, GPX3, HBA1, HBA2, HP, ITIH4, LAMC1, LTBP4, PCOLCE, PRG2, PXDN, RBP4, SERPINA6, SUSD2, TINAGL1 and TNC can be used. Since these proteins are secreted into urine, urine discharged to the outside of the body can be used as a specimen without using an invasive method with urothelium biopsy to obtain a sample (or a biological sample), and thus it is characterized by simple and rapid OAB diagnosis as a non-invasive method.

Among these, C2, C3, C4A, C4B, CFH, CILP, IGFBP7, ITIH1, MGP, NID2 or PF4 are proteins that are specifically existed or detected only in the urine of OAB subjects. There is an effect that the OAB can be determined or diagnosed by only the presence or absence of existence or the presence or absence of detection of these proteins in the urine.

The above-mentioned 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, RBP4, SERPINA6, SUSD2, TINAGL1 or TNC is a protein which is not detected in the urine of the OAB and is specifically existed or detected only in the urine of a normal subject. There is an effect that the OAB can be determined or diagnosed by only the presence or absence of existence or the presence or absence of detection of these proteins in the urine (or an effect that can be determined or diagnosed as a normal subject by distinguishing from the OAB).

More preferably, it may be preferable to use proteins which are present or detected only in the urine of the OAB subject as markers, and specifically, one or more (protein) selected from a group consisting of C2, C3, C4A, C4B, CFH, CILP, IGFBP7, ITIH1, MGP, NID2 and PF4 can be used. These proteins offer significant advantages in terms of detection convenience and increased diagnostic efficiency compared to other protein markers that are nonexistent only in OAB urine.

Markers in accordance with the present invention may be used in one or more combinations, e.g., two, three, four, five, six, seven, or more combinations. Those skilled in the art will be able to select a combination of markers that satisfy the desired sensitivity and specificity through methods such as analysis and/or a logistic regression analysis using a biological sample of a subject including a normal person and a patient.

Based on the novel diagnostic use of the above-described 52 proteins, the present invention provides a composition for the diagnosis of OAB disease comprising the agents for measuring the activity or the expression level of at least one selected from the group (the group includes all of the marker proteins and the genes encoding them [including all of the polynucleotides including the transcripts thereof]) consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2, PF4, RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC, and a kit for diagnosing OAB disease comprising the same.

The above-mentioned agent is not particularly limited as long as it can measure the activity or expression level of the marker described above, but can use (I) an antibody that specifically binds to a protein selected from the above group, and a peptide or aptamer having a binding domain specific to the protein; or (II) a primer or a probe that specifically binds to mRNA (or cDNA) of a gene encoding a protein selected from the above group.

Specifically, when the diagnostic composition of the present invention is to measure the activity or expression level of the marker protein, an agent used for the measurement may be (I) an antibody that specifically binds a marker protein selected from the group of 52 markers, and a peptide or an aptamer having a binding domain specific to the marker protein.

As used herein, the term "antibody" refers to an immunoglobulin that specifically binds to an antigenic site, as is known in the art. The antibody can be prepared according to conventional methods in the art such as injecting a specific protein (in the present invention, each of the marker proteins described above) into an animal and obtaining an antibody produced at that time. The antibody may be produced through a full-length polypeptide of each marker protein, or may be prepared using a fragment containing an antigenic site of the polypeptide. The form of the antibody of the present invention is not particularly limited and includes a polyclonal antibody or a monoclonal antibody. Also, part of the whole antibody (i.e., fragment) is included in the antibody of the present invention as long as it has antigen-antibody binding (reaction). For example, the complete forms of antibodies having two full-length light chains and two full-length heavy chains, as well as functional fragments of antibody molecules such as Fab, F(ab'), F(ab')2 and Fv having an antigen binding function are included. Furthermore, the antibodies of the present invention include special antibodies such as humanized antibodies, chimeric antibodies, and recombinant antibodies. In addition, the antibody can be purchased and used in the art.

The "peptide" means a polypeptide which does not have the structure of the antibody or fragment thereof described above but has a domain specifically binding to a specific site of a target protein (in the present invention, each marker protein described above). The length of the peptide is not particularly limited, but may be including, for example, 2 to 100 amino acids, preferably 5 to 50 amino acids.

The term "aptamer" in the present invention means a single-stranded nucleic acid (DNA, RNA, or modified nucleic acid) having a stable tertiary structure as a substance capable of specifically binding with an analyte to be detected in a sample. Thus, the presence of the target protein (polypeptide) in the sample can be confirmed specifically. The preparation of the aptamer, after determining and synthesizing the sequence of an oligonucleotide having a selective and high binding ability with respect to a target protein to be identified (each marker protein in the present invention) according to a general method of producing an aptamer, is carried out by changing into —SH, —COOH, —OH or —NH2 to allow the 5' or 3' end of the oligonucleotide to bind to the functional group of the aptamer chip, but is not limited to.

The present invention provides a kit for the diagnosis of OAB disease comprising such a measurement agent. The kit is not particularly limited as long as it is known in the art as an assay kit for providing an antibody, a peptide having a specific binding domain to a target protein, or an aptamer as a component. For example, western blotting, enzyme-linked immunospecific assay (ELISA), radioimmunoassay (RIA), Ouchterlony immunodiffusion, rocket immunoelectrophoresis, tissue immuno staining, immunoprecipitation assay, complement fixation assay, fluorescence activated cell sorter (FACS) or protein chip kit is included.

The kit may include one or more other component compositions, solutions or devices suitable for the assay in addition to an antibody recognizing the marker, a peptide having a specific binding domain in the marker protein, or an aptamer. In one example, the kit can comprise a reagent capable of detecting the bound antibody such as a labeled secondary antibody, chromophores, an enzyme (in conjugated form with the antibody) and its substrate or other substances that can bind to antibodies. In addition, the kit of the present invention may include a washing solution or an eluting solution capable of removing surplus chromogenic substrate and unbound protein and retaining only the protein marker associated with the antibody.

Also, when the diagnostic composition of the present invention is for measuring the expression level of the gene (polynucleotide, in particular mRNA) encoding the marker protein, the agent used for the measurement can comprise (II) a primer or a probe that specifically binds to the mRNA (or cDNA) of the gene encoding the marker protein selected from the 52 marker group.

The "primer" can form a base pair with a complementary template with a nucleic acid sequence having a short free 3' hydroxyl group, and refers to a short nucleic acid sequence that functions as a starting point for the template strand copy. The primer specifically binds to a polynucleotide, which is a template, under a suitable buffer and temperature conditions, and the DNA polymerase synthesizes DNA by adding nucleoside triphosphate having a base complementary to the template DNA to the primer. The primer is generally composed of 15 to 30 nucleotide sequences, and its melting temperature (Tm) varies depending on the base structure and the length. Primers can initiate DNA synthesis in the presence of reagents for polymerization (i. e., DNA polymerase or reverse transcriptase) and four different nucleoside triphosphates at appropriate buffer solutions and temperatures. The PCR conditions, the lengths of the sense and antisense primers can be appropriately selected according to techniques known in the art.

The sequence of the primer does not need to have a sequence completely complementary to a part of the nucleotide sequence of the template, and it is sufficient if the complementary part has sufficient complementarity within a range capable of hybridizing with the template and acting as a primer. Therefore, in the present invention, the primer for measuring the expression level of the mRNA of the markers does not need to have a perfectly complementary sequence to the marker gene sequence. It is sufficient if the primer amplifies a specific region of mRNA or cDNA through DNA synthesis and has a length and complementarity to the purpose of measuring the amount of mRNA. The primer for the amplification reaction consists of a pair complementarily binding to a template (or sense) and an opposite region (antisense) at opposite ends of a specific region of the mRNA to be amplified, respectively. The primers can be easily designed by those skilled in the art with reference to the marker mRNA or cDNA sequence.

The "probe" refers to a nucleic acid fragment such as RNA or DNA corresponding to a few nucleotides or several hundreds of nucleotides that can specifically bind to mRNA, and thus the presence or absence and the expression level of a specific mRNA or cDNA can be confirmed by labeling. The probe may be prepared in the form of an oligonucleotide probe, a single strand DNA probe, a double strand DNA probe, or an RNA probe. Selection of suitable probes and hybridization conditions can be appropriately selected according to techniques known in the art.

The primer or probe of the present invention can be chemically synthesized using a phosphoramidite solid support synthesis method or other well-known methods. In addition, the primer or the probe can be variously modified according to a method known in the art, so long as it does not interfere with hybridization with mRNA. Examples of such modifications include, but are not limited to, methylation, capping, substitution with one or more of the natural nucleotide analogs and modifications of nucleotides such as uncharged linkers (e.g., methylphosphonate, phosphotriester, phosphoramidate, carbamate, etc.) or charged linkers (e.g., phosphorothioate, phosphorodithioate, etc.), and the combination of labeling material using fluorescence or enzyme.

The present invention provides a kit for the diagnosis of OAB disease comprising such a measurement agent. The kind of the kit is not particularly limited as long as it is known as an assay kit that provides a primer or a probe as a component in the art. For example, a polymerase chain reaction (PCR), RNase protection assay, Northern blotting, or a kit for a DNA microarray chip is included.

The kit may include one or more other component compositions, solutions or devices suitable for the assay method in addition to the primer or probe that recognizes the marker. In one example, the kit can comprise a test tube or other suitable container, a reaction buffer (pH and various magnesium concentrations), deoxynucleotides (dNTPs), a DNA polymerase (e.g. Taq polymerase), reverse transcriptase, DNAse, RNAse inhibitor DEPC-water, sterile water, and fluorescent material.

In order to provide information necessary for the diagnosis of OAB disease, the present invention provides a method for detecting at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2, PF4, RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC (i.e., at least one selected from the above protein group or a group of genes encoding the proteins) from a biological sample isolated from a suspected subject.

In the present application, the "detection" comprises quantitative and/or qualitative analysis (measurement) and means to identify the presence or absence of the substance (marker) in the sample or to confirm the increase or decrease in the amount of the substance (marker) present in the sample. The qualitative analysis may mean measuring and confirming the presence or absence of a desired substance, and the quantitative analysis may mean measuring and confirming the change in the presence level (expression level) or the amount of a desired substance. In the present invention, the analysis or measurement can be performed without limitation, including both qualitative and quantitative methods. Such detection methods are well known in the art and will be understood with reference to the foregoing description of agents and kits comprising them that measure the activity or expression level of the 52 marker. Those skilled in the art will be able to select suitable methods and reagents for the practice of the present application.

In the present invention, the subject of the detection herein may preferably be the activity or expression level of the marker proteins selected from the above 52, or the mRNA expression levels of the genes encoding the selected marker proteins. Therefore, the detection may be performed by measuring the activity or expression level of the proteins selected from the 52 markers of the present invention, or by measuring the mRNA expression levels of the genes encoding the selected proteins.

Specifically, the detection (measurement) of the activity or expression levels of the marker proteins can be performed by any one selected from the group consisting of, for example, Western blotting, enzyme-linked immunospecific assay (ELISA), radioimmunoassay (RIA), Ouchterlony immunodiffusion, rocket immunoelectrophoresis, tissue immuno staining, immunoprecipitation assay, complement fixation assay, fluorescence activated cell sorter (FACS) or protein chip kit, and the method of detection (measurement) in the present invention is not particularly limited as long as it is the measurement method of a protein expression known in the art.

In protein expression, increased expression levels of proteins usually result in increased levels of the activity of these proteins, so that with the exception of special circumstances such as the case of mutagenesis, it will be understood by those skilled in the art that the methods described above can be used to evaluate the degree of activity of a protein. In addition, when the activity of a specific protein is detected at a high level except for a special situation such as the case of mutation occurrence, it is general that the presence level (i.e., expression level) of the protein is increased. In addition to the above-mentioned, it is also understood apparently by those skilled in the art that the level of expression (i.e., the level of expression) of a protein can be assessed depending on the activity intensity (intensity or degree) that induces a specific response to the subject material through an enzymatic method.

In addition, methods for detecting (measuring) changes in the activity of the protein itself can be performed. It may utilize the known activity of the desired protein (the marker protein). For example, it may be to use the activity of binding to a specific ligand or receptor, the enzyme-substrate specificity, the activity of catalyzing a specific reaction, the activity of hydrolyzing a specific substance, the activity of biosynthesizing a specific substance, and the activity of oxidizing/reducing a specific substance. Depending on the type of each activity, it can be measured using methods known in the art and a kit including a reaction product used for measurement and a coloring material for calculating the result is commercially available in the art.

Particularly, in the case of measuring the activity (i.e., binding ability) of directly binding to a specific object such as a ligand, a substrate or a receptor, in addition to the above-described assay method including various binding assays known in the art, it is are known in the art that methods such as a microphysiometer, real-time bimolecular interaction analysis (BIA), a cell (typically, yeast), hybrid-system analysis or a three-hybrid system assays can be used. This will be discussed in more detail below.

In addition, the detection (measurement) of mRNA expression level of the marker gene may be performed by using any one selected from the group consisting of PCR, RNase protection assay, northern blotting and DNA chip. However, the method of detection (measurement) in the present invention is not particularly limited as long as it is the method for measuring mRNA or cDNA expression known in the art.

In the present invention, the phrase "increase of the expression level (or expression amount)" means that a particular subject exhibits a marked increase over a certain level of expression in a normal state. In the present invention it is meant that the substance (particularly, each marker protein) which has been confirmed not to exist in the specific sample in the existing (especially, normal state) state is found to be present in the sample in the disease state.

In the present invention, the term "decrease of the expression level (or expression amount)" means that a specific object exhibits a remarkable reduction in a level lower than a certain level of expression in a normal state. In the present invention, it is meant that the substance (particularly, each marker protein) which has been confirmed to exist in the specific sample in the existing (especially, normal state) state is not found to be present in the sample in the disease state.

The "biological sample" is as described above. In the present invention, the term "control group" may mean a normal subject without OAB disease or a sample obtained from the normal subject.

In addition, the method may further comprise comparing (2) the detected result from the suspected subject through (1) performing the detection with the detected result of the control group (normal subject).

As a preferred embodiment, the present invention provides (1) measurement of the activity or expression level of at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2, PF4, RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC from the biological samples isolated from the suspected subject; And (2) a method for providing information necessary for diagnosis of overactive bladder disease (hereinafter, OAB diagnostic method) comprising comparison of the measurement result of the (1) with a measurement result for a normal subject.

In the case where the OAB diagnostic method further comprises (2) comparison of the detected result with the control group in the detection (1) described above, when at least one protein selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2 and PF4; or the expression level of at least one selected from the group consisting of the gene encoding the protein is up-regulated or the activity level is higher than that of the control (normal), it can be determined that the overactive bladder disease has developed or is highly likely to develop.

In addition, when at least one protein selected from the group consisting of RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC; or the expression level of at least one selected from the group consisting of the gene encoding the protein is up-regulated or the activity level is lower than that of the control (normal), it can be concluded that the overactive bladder disease has developed or is highly likely to develop.

As a more preferred embodiment of the present invention, the OAB diagnostic method of the present invention can be determined to be that the OAB disease has developed or is likely to develop when one or more selected from the group consisting of ENTPD1, VAMP2, EIF4B, PTMA, C2, C3, C4A, C4B, CFH, CILP, IGFBP7, ITIH1, MGP, NID2 and PF4 is detected (that is, it is confirmed to be present) from the biological sample (in particular, urothelium and/or urine) in the detection (in the (1)). These proteins are proteins that are specifically present or detected only in urothelium and/or urine of OAB, and have remarkable diagnostic value.

In addition, when the protein of Anxa5, Slc12a7, Vamp8, Cacna2d1, Lgals3 bp, Pgrmc1, P2RX1 or ATP5B is used as a marker, the (2) comparison with the detected result by the same method in the control group (normal subjects) may be additionally required. Even when 23 genes of the above-mentioned markers whose expression levels are increased in the OAB (meaning including all the polynucleotides including the transcript thereof, particularly mRNA) are to be detected, it may be necessary to compare the overexpression of these genes with the results in the control group. In these cases, it is possible to determine the onset or the possibility of OAB when the expression level (or detection level) of the marker is increased in a suspected subject through comparison with a control group.

In another preferred embodiment, the OAB diagnostic method of the present invention can be determined to be that the OAB disease has developed or is likely to develop when one or more selected from the protein group consisting of RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC is not detected from the biological sample (in particular, urothelium and/or urine) in the detection (in the (1)). Conversely, when these proteins are detected, it can be determined that the OAB has not been or is not likely to develop (normal). These proteins are proteins that are specifically present or detected only in the urothelium and/or urine of normal subjects, and have remarkable diagnostic value.

In the case where the above-mentioned 29 kinds of marker genes (in particular, mRNA) are to be detected, it may be necessary to compare the low expression of these genes with the results in the control group. In this case, it is possible to determine the onset or the possibility of OAB when the expression level (or the detection level) of the marker is decreased in a suspected subject through comparison with a control group.

It can be determined that the OAB disease is likely to develop or the disease is already progressing or deepening depending on the degree of increase or decrease of the expression level of the markers. The degree of increase or decrease in the activity or expression level on which the diagnosis is based can be determined by dividing the degree of expression level according to the technique known in the art in accordance with the measurement method used. For example, by measuring the expression level of each marker from a large number of normal and patient samples, accumulating and analyzing the data, the criteria may be divided into the normal category, disease severity classification, or onset of symptoms depending on the degree of expression level to provide an appropriate diagnostic criterion.

The expression pattern of the 52 kinds of proteins (and the genes encoding them) for the OAB identified in the present invention also provides a screening strategy for agents that can have the preventive and therapeutic effects of OAB disease.

First, in order to select a drug (substance) capable of preventing or treating OAB in an inhibitor system, the present invention provides a drug screening method for the prevention or treatment of overactive bladder disease, comprising (A) culturing cells expressing at least one selected from the group consisting of Anxa5, Slc12a7, Vamp8, Cacna2d1, Lgals3 bp, Pgrmc1, ENTPD1, P2RX1, ATP5B, VAMP2, EIF4B, PTMA, C2, C3, C4A, C4B, CFH, CILP, IGFBP7, ITIH1, MGP, NID2 and PF4 with or without a test agent; And (B) comparing the degree of expression or activity of the proteins selected in step (A) in the cells cultured with the test agent and the cells cultured without the test agent, and thus confirming whether the test agent inhibits the expression or activity of the proteins selected in step (A).

After step (B), the screening method may further comprise (C) administering a test agent that has been found to have an effect of inhibiting expression or activity in step (B) to an animal having overactive bladder disease to determine whether the test agent exhibits a therapeutic effect.

The present inventors have found that the expression levels of the above-mentioned 23 markers are specially increased in the OAB disease state. Therefore, it is definitely understood that the agent (test agent) that results in inhibiting (reducing) the expression and/or activity of at least one selected from the group consisting of the above-mentioned 23 marker without limiting the specific mechanism can be expected to have an effect of improving, treating or preventing the condition of OAB disease in those skilled in the art.

The term "inhibitor" in the present invention means a substance which includes all of an inhibitor of activity or an inhibitor of expression, and which partially inhibits or completely (substantially completely) inhibits (blocks) activity or expression. The inhibitor can act directly or indirectly on the object of interest, and can include a single compound such as an organic or inorganic compound, biopolymer compound and a complex of a plurality of compounds such as a peptide, a protein, a nucleic acid (polynucleotide), a carbohydrate and a lipid.

For example, the activity inhibitor may be one that competitively or non-competitively binds to the 23 proteins described above to reduce activity (such as signal transduction), and may include an antibody that specifically binds to the protein, but is not limited thereto.

For example, the expression inhibitor refers to a substance that acts in a manner that inhibits protein synthesis at any point in the total process including transcription and translation for protein synthesis, and its type is not particularly limited, but, for example, includes antisense RNA, siRNA and miRNA. As a specific example, the regulation at the transcription stage may be performed by a method for inhibiting expression of the gene known to a person skilled in the art, and, for example, it may include a method of inducing a mutation of a promoter or a gene region to inhibit a promoter activity or a function of a protein, a method of expressing an antisense gene as described above, an iRNA method (iRNA refers to a variety of forms or names of interfering RNAs known in the art such as siRNA, or shRNA), or a microRNA method. In another example, regulation at post-transcription can be accomplished by methods that inhibit the expression of proteins known to those skilled in the art, and, for example, it may include a method that inhibits the stability of the transcribed mRNA, or inhibits the stability of the protein or polypeptide.

As used herein, the term "treatment" or "treating" refers to inhibition of disease development, inhibition of recurrence, alleviation of symptoms, reduction of direct or indirect pathological consequences of disease, a reduction in the rate of disease progression, an improvement in the disease state, an improvement, or alleviation.

The term "prevention" or "preventing" used in the present invention refers to any action that inhibits the onset of disease or delays its progression.

In addition, in order to select a drug (substance) capable of preventing or treating OAB in an inhibitor system, the present invention provides a method for screening an agent for the prevention or treatment of overactive bladder disease, comprising (a) culturing a cell expressing at least one selected from the group consisting of RBP4, RPSA, PIN2, CP, SOD2, HSPD1, PEF1, 1300017J02Rik protein, A1BG, CFL2, CPA3, ECM1, FBLN5, FGB, FMOD, GPX3, HBA1, HBA2, HP, ITIH4, LAMC1, LTBP4, PCOLCE, PRG2, PXDN, SERPINA6, SUSD2, TINAGL1 and TNC with or without a test agent; And (b) comparing the degree of expression or activity of the protein selected in step (a) in the cells cultured with the test agent and the cell cultured without the test agent, thereby confirming whether the test agent increases the expression or activity of the protein selected in step (a).

After step (b), the screening method may further comprise (c) administering a test agent that has been found to have an effect of increasing expression or activity in step (b) to an animal having overactive bladder disease to determine whether the test agent exhibits a therapeutic effect.

The present inventors have found that the expression levels of the above-mentioned 29 markers are specially decreased in the OAB disease. Therefore, it is definitely understood that the agent (test agent) that results in increasing (promoting) the expression and/or activity of at least one selected from the group consisting of the above-mentioned 29 marker without limiting the specific mechanism can be expected to have an effect of improving, treating or preventing the condition of OAB disease in those skilled in the art.

The term "activator" in the present invention refers to a substance that increases, induces, or stimulates activity or expression, including all of promoter (enhancer) of the activity or promoter (enhancer) of expression. The activator can act directly or indirectly on the object of interest, and can include a single compound such as an organic or inorganic compound, biopolymer compound and a complex of a plurality of compounds such as a peptide, a protein, a nucleic acid (polynucleotide), a carbohydrate and a lipid.

For example, the activator may be one that competitively or noncompetitively binds to one or more proteins selected from the 29 types of markers described above, or to polynucleotides encoding the marker proteins to increase activity (such as signal transduction), and also act in a manner that increases protein synthesis at any point in the total process including transcription and translation for protein synthesis, but the specific type thereof is not particularly limited.

In the two-way screening method described above, the cells used in the screening may be cells that naturally express the markers, or may be genetically engineered to express the markers using genetic methods known in the art. For example, the recombinant expression vector may be used to express the marker in the cell by transformation, which will be described in detail above.

The specific type of the cells used in the screening is not particularly limited, but there is a possibility of using eukaryotic cells, and more preferably cells of tissues forming the bladder. Most preferably, it can be the urothelium of the bladder.

The term "agent" or "test agent" in the present invention comprises any substance, molecule, element, compound, entity or any combination thereof. For example, it includes, but is not limited to, a protein, a polypeptide, a small organic molecule, a polysaccharide, and a polynucleotide. It may also be a natural product, a synthetic compound or chemical compound, or a combination of two or more substances. Unless otherwise specified, the agents, materials and compounds may be used interchangeably.

Test agents that can be screened or identified by the methods of the present invention include, but are not limited to, polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, saccharides, fatty acids, purines, pyrimidines or derivatives, structural analogs or combinations thereof. Some test agents may be synthetic and other test agents may be natural. The test agents may be obtained from a wide variety of sources including libraries of synthetic or natural compounds. A combinatorial library can be produced with a variety of compounds that can be synthesized step-by-step. Compounds of multiple combinatorial libraries can be prepared by the encoded synthetic libraries (ESL) method (WO 95/12608, WO 93/06121, WO 94/08051, WO 95/395503 and WO 95/30642). Libraries of natural compounds in the form of bacterial, fungal, plant and animal extracts can be obtained from commercial sources or collected in the field. Known pharmacological agents can be applied to direct or random chemical modifications such as acylation, alkylation, esterification, or amidification to produce structural analogs. The test agent may be a naturally occurring protein or a fragment thereof. Such test agents can be obtained from natural sources such as cell or tissue lysates. Libraries of polypeptide agents can be obtained, for example, by conventional methods or from commercially available cDNA libraries. The test agent may be a peptide, for example, having about 5-30 amino acids, preferably about 5-20 amino acids, more preferably about 7-15 amino acids. The peptide may be a naturally occurring protein, a random peptide or a cleavage of a "biased" random peptide.

The test agent may also be "nucleic acid." The nucleic acid test agent may be a naturally occurring nucleic acid, a random nucleic acid, or a "biased" random nucleic acid. For example, the cleavages of prokaryotic or eukaryotic genomes can be used similar to those described above.

The test agent may also be a small molecule (e.g., a molecule having a molecular weight of about 1,000 or less). A high throughput assay can be preferably applied to the method for screening the small molecule control agent. A combination library of small molecule test agents as described above can be easily applied to the screening method of the present invention. Many assays are useful for screening (Shultz, Bioorg. Med. Chem. Lett., 8:2409-2414, 1998; Weller, Mol. Drivers., 3:61-70, 1997; Fernandes, Curr. Opin. Chem. Biol., 2:597-603, 1998; and Sittampalam, Curr. Opin. Chem. Biol., 1:384-91, 1997).

The screening of the present invention can be performed by a variety of biochemical and molecular biological techniques known in the art, and such techniques are disclosed in the following references: Sambrook et al., Molecular Cloning: A Laboratory Manual, Cold Spring Harbor Press, N.Y., Second (1998) and Third (2000) Editions; and Ausubel et al., Current Protocols in Molecular Biology, John Wiley & Sons, Inc., New York (1987-1999).

A library of test agents screened in the methods of the present invention can be prepared based on the structural studies of each of the above-mentioned proteins (marker proteins in the present invention) or analogues thereof. Such structural studies enable the identification of test agents that could be bound to the above-mentioned proteins. The three-dimensional structure of proteins can be studied in a number of ways such as crystal structure and molecular modeling. Methods for studying protein structures using X-ray crystallography are well known in the literature: Physical Biochemistry, Van Holde, K. E. (Prentice-Hall, New Jersey 1971), pp. 221-239, and Physical Chemistry with Applications to the Life Sciences, D. Eisenberg & D. Crothers (Benjamin Cummings, Menlo Park 1979). Computer modeling of protein structures provides other means for the design of test agents for screening. Molecular modeling methods are described in the literature: U.S. Pat. No. 612, 894 and U.S. Pat. No. 5,583,973. The protein structure can also be determined by neutron diffraction and nuclear magnetic resonance (NMR): Physical Chemistry, 4th Ed. Moore, W. J. (Prentice-Hall, New Jersey 1972) and NMR of Proteins and Nucleic Acids, K. Wuthrich (Wiley-Interscience, New York 1986).

In the present invention, "culturing a cell expressing at least one selected from the group with the test agent" means a process of inducing the contact of the test agent with the marker protein itself and/or factors affecting its expression. The contacting method of the test agent may be, for example, one in which the test agent is treated outside the cell membrane and introduced into the cell in vitro, or one in which the test agent is expressed in cells by known standard recombinant DNA and molecular cloning techniques, but is not limited to.

The "comparison of the level of expression or activity (level)" is meant to include both the measuring (detecting) and comparing the degree of expression or activity of the subjects selected as the markers in the previous step for each experimental group (test agent of treatment group) and/or the control group (test agent of non-treatment group). Specifically, the subject of the measurement may preferably be, but is not limited to, the activity or expression level of the marker protein selected above, or the mRNA expression level of the gene encoding the marker protein selected above. These measurement methods are described above.

Particularly, in order to screen for drugs that induce only the change (decrease or increase) in the activity of the protein itself rather than the expression level of the protein, the substances inhibiting activity of the target protein (the marker in the present invention) by other factors (e.g., binding to upstream regulatory elements) or binding to the target protein may be screened. In the latter case, any type of marker protein, such as a separated marker protein or a marker protein contained in a cell, may be used. As a screening method using this method, the present invention can be carried out in a high throughput manner, in particular according to various binding assays known in the art.

In this screening method of the present invention (particularly, the method using binding analysis), the test substance or the selected marker protein may be labeled with a detectable label. For example, the detectable label may be a chemical label (e.g., biotin), an enzyme label (e.g., horseradish peroxidase, alkaline phosphatase, peroxidase, luciferase, β-galactosidase, and α-glucosidase), radioactive labels (e.g., $^{14}C$, $^{125}I$, $^3P$ and $^{35}S$), fluorescent labels (e.g., coumarin, fluorescein, and fluoresein isothiocyanate (FITC), rhodamine 6G, rhodamine B, 6-carboxy-tetramethyl-rhodamine (TAMRA), Cy-3, Cy-5, Texas Red, Alexa Fluor, DAPI(4,6-diamidino-2-phenylindole), HEX, TET, Dabsyl and FAM, luminescent label, chemiluminescent label, a fluorescence resonance energy transfer (FRET) label or a metal label (e.g., gold and silver).

When a desired protein (a marker protein selected in the present invention) or test substance labeled with a detectable label is used, the binding or not between the desired protein and the test substance can be detected by detecting the signal from the label. For example, when alkaline phosphatase is used as a label, the signal is detected using a chromogenic substrate such as bromochloroindole phosphate (BCIP), nitroblue tetrazolium (NBT), naphthol-AS-B1-phosphate and enhanced chemifluorescence (ECF). When horseradish peroxidase is used as a label, the signal is detected using a substrate such as chlorinaphthol, aminoethylcarbazole, diaminobenzidine, D-luciferin, lucigenin (bis-N-methyl acridinium nitrate), resorpine benzyl ether, luminol, Amplex red reagent (10-acetyl-3, 7-dihydroxy phenoxazine), HYR (p-phenylenediamine-HCl and pyrocatechol), tetramethylbenzidine (TMB), 2,2'-Azine-di [3-ethylbenzthiazoline sulfonate] (ABTS), o-phenylenediamine (OPD) and naphthol/pyronin.

Alternatively, the binding of the test substance to the desired protein (the marker protein selected in the present invention) may be assayed without labeling of the interactants. For example, a microphysiometer can be used to analyze whether a test substance binds to a desired protein (a marker protein selected in the present invention). The microphysiometer is an analytical tool that uses a light-addressable potentiometric sensor (LAPS) to measure the rate at which a cell acidifies its environment. A change in the rate of acidification can be used as an indicator of the binding between the test substance and the desired protein (a marker protein selected in the present invention) (McConnell et al., Science 257: 19061912 (1992)).

The ability of the test substance to bind to the desired protein (the marker protein selected in the present invention) can be analyzed using real-time bimolecular interaction assay (BIA) (Sjolander & Urbaniczky, Anal. Chem., 63: 2338-2345 (1991), and Szabo et al., Curr. Opin. Struct Biol. 5: 699-705 (1995)). BIA is a technique for analyzing specific interactions in real time and can be carried out without the labeling of interactants (e.g., BIAcore™). Changes in surface plasmon resonance (SPR) can be used as an indicator of the real-time response among molecules.

In addition, the screening method of the present invention can be carried out according to a two-hybrid analysis or a three-hybrid analysis method for cells (typically yeast) (U.S. Pat. No. 5,283,317; Zervos et al., Cell 72, 223232, 1993; Madura et al., J. Biol. Chem. 268, 1204612054, 1993; Bartel et al., BioTechniques 14, 920924, 1993; Iwabuchi et al., Oncogene 8, 16931696, 1993; and WO 94/10300). In this case, the desired protein (the marker protein selected in the present invention) can be used as a "bait" protein. According to this method, a substance binding to a desired protein, particularly a protein, can be screened. Two-hybrid system is based on the modular nature of the transcription factor consisting of divisible DNA-binding and activation domains. Briefly, this analysis method uses two DNA constructs. For example, in one construct, a desired protein (a marker protein selected in the present invention)-coding polynucleotide is fused to a DNA binding domain-coding polynucleotide of a known transcription factor (e.g., GAL4). In other constructs, a DNA sequence encoding the protein ("prey" or "sample (test agent)") of interest to be analyzed is fused to a polynucleotide encoding the activation domain of the known transcription factor. If bait and prey interact in vivo to form a complex, the DNA-binding and activation domains of the transcription factor become adjacent, which triggers the transcription of a reporter gene (e.g., LacZ). Expression of the reporter gene can be detected, which indicates that the protein to be analyzed can bind to the desired protein (the marker protein selected in the present invention), and through this binding, it is possible to control (increase or decrease) the activity of the target protein, and consequently it can be used as a preventive and therapeutic agent for OAB disease of cells.

It is preferable that an animal having the OAB disease animal used in the (C) or (c) of inspection further included in the screening method is a non-human animal.

The markers described in the present invention can effectively detect or diagnose the onset of OAB by distinguishing them from normal populations. In particular, OAB-specific protein markers released into urine enable simple and rapid OAB diagnosis in a non-invasive manner. In addition, by selecting an agent that changes (particularly normalizes) the expression (and activity) of the markers selected in the present invention, more effective prevention or treatment of OAB disease can be screened.

Hereinafter, preferred Examples will be provided to facilitate understanding of the present invention. However, the following Examples are provided for better understanding of the present invention only, and the scope of the present invention is not limited by the following Examples.

Experimental Method

1. Experimental Animals

All animal studies follow guidelines for animal care and use, and the protocol has been approved by the Institutional Animal Care and Use Committee of Chungnam National University, Daejeon, Korea (IRB No. CNU-00706). In this study, female Sprague-Dawley rats (200±30 g) were used. In this study, animals were divided into two groups: Animals were given a standard rat chow diet to a sham-operated group (n=40) and a partial bladder outlet obstruction group (n=60) and water was free-watered. In standard laboratory conditions (25±1° C., 55±5 ?humidity, and 12-hour light-dark cycle changes), the animals were individually housed with sawdust placed in separate cages.

2. Surgical Induction of Partial Bladder Outlet Obstruction

To induce a partial obstruction of the urethra, conventional surgical procedures such as those described in "Lluel P. et al., (1998)" and "Lee, T., et al., (2008)" were performed. The rats were anesthetized with intramuscular injection of xylazine (10 mg/kg) and ketamine (100 mg/kg). To reduce heat loss during surgery, the rats were placed in a servo-controlled surgical table. The lower midline incision was used to expose the bladder and proximal urethra. After confirming the urethra, a 0.9 mm diameter steel rod was inserted from the meatus into the urethra. 4-0 Novafil ligature (monofilament polybutester; Davis & Geck, Wayne, N.J.) was placed around the urethra to be tied at the steel frame position and constantly add ligation tension. After suturing, the urethra was partially clogged by removing the steel frame. The sham procedure also proceeded in a similar manner, and a 4-0 non-absorbable monofilament suture was loosely tied around the dissected urethra.

3. Insert Catheter

Intravesical catheter insertion was performed 3 days before the cystometry procedure. A polyethylene catheter (PE-20; AM Systems, Carlsberg, Wash., USA) with a cuff was inserted into the bladder dome through a lower abdominal incision and fixed with a purse-string suture in a 6-0 silk thread. The catheter creates a tunnel under the skin, fixed with a 4-0 silk thread and exteriorized at the level of the superior scapula. The free end of the catheter was sealed for 3 days. In the peritoneal and muscle incision, the incision site was closed with a continuous 5-0 vicryl suture and a 5-0 silk suture was used for skin suture. The same procedure was applied to the sham-operated rats.

4. Bladder Cystometry

On the 14th day after the first operation, bladder cystometry was performed without anesthesia. To measure intravesical pressure (IVP), the end of the catheter in the bladder during the bladder cystometry was connected to a pressure transducer (PowerLab, AD Instrument, Sydney, Australia) and a grouting pump (Promed-Tech., Bellingham, Mass., USA), and saline at room temperature was injected into the bladder at 10 ml/h. Conscious rats were placed in metabolic cages in which water and feed were supplied freely. The cage was also capable of measuring micturition volume (MV) using a fluid collector and the fluid collector was connected to a force displacement transducer (Grass Instruments, Quincy, Mass., USA) which was connected to data acquisition software (PowerLab, AD Instrument) through a transducer amplifier. After stabilizing the urine pattern, data were collected for 4-6 representative urination cycles and the mean value was calculated. Using a Windows Data Acquisition System (PowerLab, AD Instrument) Chart v 5.5.6, IVP and MV were recorded simultaneously and continuously at a sampling rate of 2000 Hz.

After urination, saline infusion was stopped, and the residual urine volume (RV) was extracted through a tube inserted into the bladder using a syringe for bladder cystometry. In addition, the below-mentioned parameters of the pressure inside of the bladder were examined: the pressure inside of the bladder and volume parameters including basal pressure (BP, the lowest bladder pressure between two urination), micturition pressure (MP, maximum bladder pressure during urination), threshold pressure (TP, bladder pressure at the onset of urination), intermicturition pressure (IMP, mean bladder pressure between two urination), spontaneous activity (SA, IMP-BP), micturition interval (MI), micturition volume (MV), bladder capacity (BC, MV+RV) and voiding efficiency (VE, MV/BC) were examined. Detrusor overactivity was defined as an apparent increase in urination and/or non-urination contractions, and non-urination contractions were defined as elevation of IVP from basal pressure without discharge of fluid from the urethra.

5. Preparation of Urothelium Tissue for Urinary Bladder

After the bladder cystometry, the rats were anesthetized and the bladder was removed near the proximal urethra via an abdominal incision. The bladder tissue was weighed and the lamina propria was dissected under a dissecting microscope to carefully separate the urothelium from the smooth muscle layer. For biochemical measurements, each of the samples obtained was immediately stored at −70° C.

6. Protein Extraction, SDS-PAGE and in-Gel Digestion

For proteomic analysis, 10 bladder urothelium tissues were put into two tubes for each group. The bladder urothelium tissue samples were homogenized with micropestle with 700 μL lysis buffer containing 8 M urea and protease inhibitor cocktails. Tissue debris was removed by low speed centrifugation at 2,000×g for 10 min and the supernatant was collected. Protein concentration was determined by bicinchoninic acid (BCA) method and samples were stored at −70° C. for further study. 15 μg of protein sample was separated by 12% SDS-PAGE. The gel was stained with Coomassie Brilliant Blue R-250. In-gel digestion can be performed according to previously described method in Park, E. C. et al. (2012). The gel was fractionated into 8 portions according to molecular weight. After the gel fragment was destained, the cysteine of the protein was reduced and alkylated and then digested with trypsin at 37° C. for 16 hours. The digested peptides were extracted with extraction solution (50 mM ammonium bicarbonate, 50% acetonitrile, and 5 trifluoroacetic acid). The digested peptides were dissolved in 10 μl of sample solution containing 0.02 formic acid and 0.5 & acetic acid.

7. Protein Identification by LC-MS/MS Using LTQ-Velos Mass Spectrometry

The peptides were isolated (identified) using liquid chromatography integrated with electrospray ionization mass spectrometry (LC-ESI MS). The peptide sample (5 μl) was concentrated on a 75 μm ID trapping column filled with 5 μm C18 particles (Acclaim PepMap100, Thermo Scientific), and analyzed on a 15 cm analysis column (Acclaim PepMap RSLC, Thermo Scientific) filled with 2 μm m C18 particles. Reversed phase chromatography was performed using Ultimate 3000 RSLC nanosystems (Thermo Scientific) with binary solvent containing 0.1% formic acid (solvent A) and 80% ACN (in 0.1% formic acid, solvent B). Peptides were isolated under linear gradient conditions of solvent B from 5% to 95% for 100 mins at 300 nl/min flow rate. All MS and MS/MS spectra of the LTQ-Velos ESI ion trap mass spectrometer (Thermo Scientific, USA) were collected in data-dependent mode. Three MS/MS scans of the richest precursor ions in the MS spectrum were followed in the MS spectrum where dynamic exclusion is possible after each full MS (m/z range 300-2000) scan. MS/MS analysis was performed three times for each sample. The raw MS/MS spectral files were converted to mgf files using the Proteome Discoverer daemon ver.1.4 (Thermo Fisher Scientific, Waltham, Mass., USA). The converted mgf file was used to identify proteins using MASCOT ver.2.4.0 (Matrix science, www.matrixscience.com). The protein quantification value was obtained by calculating exponentially modified protein abundance index protein quantification (emPAI). The search parameters applied to the database search were as follows:

enzyme specificity: trypsin/P; maximum missed cleavages: 2; carboxymethyl (C) as a static modification; oxidation (M) and N-terminal acetylation as dynamic modifications; a precursor mass tolerance of 0.8 Da; and a MS/MS mass tolerance of 0.8 Da. The MS/MS data were filtered according to the FDR (false discovery rate, calculating the false positive match ratio in the Decoy database among matching numbers in the database)<1% criterion. The UniProt rat proteome database (2015_01, www.uniprot.org) was used as a database for protein identification.

8. Bioinformatics Analysis

Functional analysis of the data set was performed using Ingenuity Pathway Analysis (IPA, Ingenuity Systems, Redwood City, Calif., www.ingenuity.com). The most important biological functions and/or diseases in the data set were identified through functional analysis. The analysis was performed on the Ingenuity Knowledge Base. The Fischer's exact test was used to calculate the p-value, which determines the probability that each biological function and/or disease assigned to each data set is due to chance. The most important pathway in the data set was confirmed from the Ingenuity Pathway Knowledge Base through canonical pathway analysis. The significance of the relevance between the data set and the canonical pathway is measured by the ratio of the number of proteins from the data set mapped to canonical pathway to the total number of proteins mapped to the canonical pathway and by Fisher's exact test. The focus genes from the two short lists were overlaid on the global molecular network developed on the basis of the information contained in the Ingenuity Pathway Knowledge Base. This created a network based on the relevance of individual proteins. At the same time, a cluster of proteins and differentially expressed genes were generated.

9. Statistical Analysis

Data were expressed as mean±SEM (standard error of the mean). All statistical analyzes were performed using Predictive Analytics Software 18.0 (SPSS Inc., Chicago, Ill., USA). Statistical analysis was performed with Student's t-test and Mann-Whitney U-test when data were not normally distributed. If the null hypothesis could be rejected with >95% confidence, the difference was considered statistically significant (p<0.05).

10. Western Blot, Immunohistochemistry and Quantitative RT-PCR

Western blotting and immunohistochemical staining were performed according to standard protocols known in the art, such as Park, E. C. et al, (2012). The primary antibodies used were: R-actin (sc-47778), P2RX1 (sc-25692), ATP5B (sc-33618), VAMP2 (sc-13992), EIF4B (sc-82587), PTMA (sc-30037). Total RNA extraction and cDNA synthesis were performed as described in the literature, such as Park, E. C. et al., Real-time PCR was performed on Exicycler™ 96 (Bioneer, Daejeon, S. Korea) using SYBR Green.

Example 1: Establishment of Mouse Model Having OAB (Overactive Bladder) Disease

It is well known that OAB can be induced by bladder outlet obstruction (BOO), and especially when there is benign prostate hyperplasia, symptoms of bladder outlet obstruction appear and OAB disease is often accompanied by it. Because the effect of bladder outlet obstruction in humans can be induced surgically in animal models, an animal model having a partial bladder outlet obstruction was used in the OAB study. To investigate the protein expression profile of OAB urothelium, OAB mouse models were constructed. Partial bladder outlet obstruction was induced by a surgical procedure that bound the urethra of the rat. A significant increase in bladder weight was observed in the OAB group compared to the control group (Table 1).

TABLE 1

Results of bladder weight and cystometric analysis in experimental animals (Infusion rate = 10 ml/h)

| Group | sham | OAB | p-values |
|---|---|---|---|
| bladder weight (mg) | 105.5 ± 9.4 | 194.7 ± 12.8 | <0.001 |
| Micturition interval (MI) (min) | 8.76 ± 1.27 | 4.8 ± 0.4 | <0.01 |
| Micturition volume (MV) (ml) | 1.43 ± 0.12 | 0.78 ± 0.08 | <0.001 |
| Residual volume (RV) (ml) | 0.03 ± 0.01 | 1.86 ± 0.19 | <0.001 |
| Bladder capacity (BC) = MV + RV) (ml) | 1.46 ± 0.12 | 2.64 ± 0.17 | <0.001 |
| Basal pressure (BP) (cmH$_2$0) | 14.3 ± 1.6 | 17.5 ± 2.4 | <0.05 |
| Threshold pressure (TP) (cmH$_2$0) | 25.9 ± 4.1 | 36.2 ± 4.9 | <0.01 |
| Maximal micturition pressure (MP) (cmH$_2$0) | 53.8 ± 6.3 | 68.5 ± 7.5 | <0.05 |
| Intermicturition pressure (IMP) (cmH$_2$0) | 18.4 ± 2.1 | 23.4 ± 3.8 | >0.05 |
| Spontaneous activity (SA = IMP-BP) (cmH$_2$0) | 4.1 ± 0.3 | 5.9 ± 0.4 | <0.001 |
| Voiding efficiency (VE = MV/BC) | 0.98 ± 0.01 | 0.30 ± 0.04 | <0.001 |

Figure 1B:
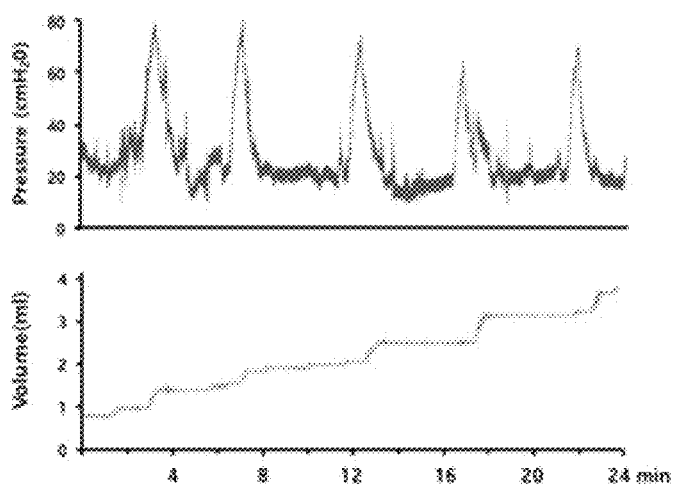

A representative pressure inside of the bladder follow-up result in the Sham surgical and OAB group rats is shown in FIG. 1. An unstable basal pressure pattern was observed in the OAB group, the pressure was higher than the control, and the micturition interval in the OAB group was significantly shortened. The residual urine volume after urination was significantly increased in the OAB group compared with the control group, and the micturition volume (MV) was significantly decreased. Cystometry of the OAB group showed a significant increase in threshold pressure and spontaneous bladder activity increased with frequent urination. In the OAB group, the maximal micturition pressure was significantly increased and the voiding efficiency was decreased (See FIG. 1 and Table 1). These results support that the OAB model showing detrusor overactivity was prepared through the above-mentioned bladder outlet obstruction surgery. This experimental model reflects bladder outlet obstruction due to a variety of causes and concomitant impairment status associated with OAB development, and particularly, the impairment status of the urinary organs including the bladder, urethra, etc., with regard to the benign prostate hyperplasia.

Example 2: Identification of Proteins Associated with OAB

Figure 2:
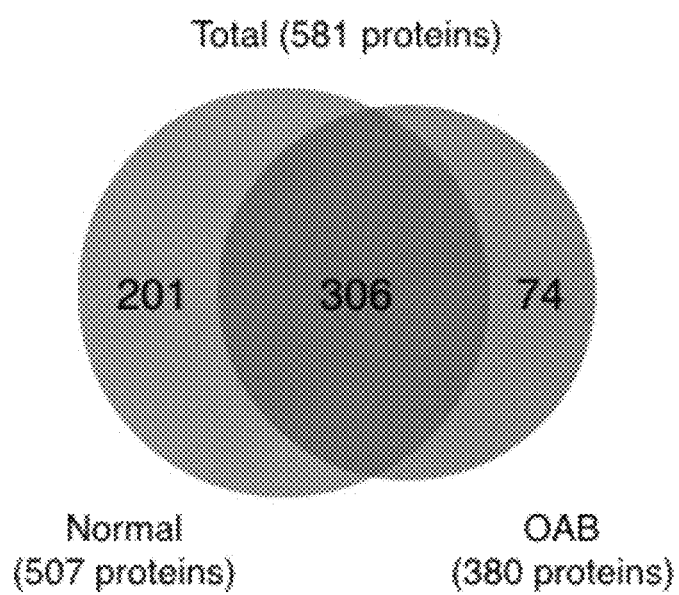
FIG. 2 shows a Venn diagram showing the number of proteins identified in normal and OAB rats in the urothelium.

To examine the difference in protein expression between the urothelium of the sham control bladder and OAB urothelium, urothelium was carefully removed from the smooth muscle layer. Proteins were extracted and analyzed using the LTQ-Velos ESI ion trap mass spectrometer. A total of 507 proteins were detected in urothelium of sham control rats and 380 proteins were detected in urothelium of OAB rats (See FIG. 2).

Of these, 306 (52.7%) proteins were generally expressed in urothelium of sham control and OAB. By contrast, 201 proteins were found in the sham control urothelium and 74 proteins were found in the OAB urothelium, respectively. A large number of proteins expressed in the sham control urothelium (201 out of 507 (39.6%)) were found to be inhibited in the OAB urothelium. 19.5% (74 of 380) of proteins were expressed in the OAB urothelium, but not expressed in the sham control urothelium (See FIG. 2 and Table 2). Also, the expression level of 80 (52+28, 26.1%) of the 306 proteins expressed in general was changed by at least 2.0 times or more (Table 2). This suggests that the protein expression of urothelium in OAB disease changes markedly and the function of normal urothelium is destroyed in OAB rat model. Finally, as shown in Table 2 below, a total of 355 proteins consisting of proteins (201 proteins) detected only in normal (sham proteins), proteins detected in OAB (74 proteins), and proteins markedly changing more than twice in OAB (80 proteins) were differentially expressed in OAB.

Figure 3A:
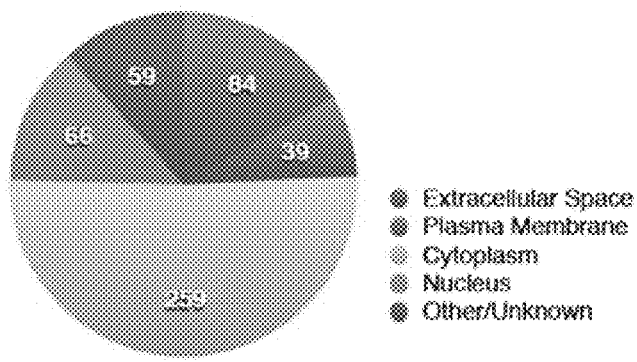
FIG. 3A and FIG. 3B show the results of classifying the subcellular localization of the identified protein.
Figure 3B:
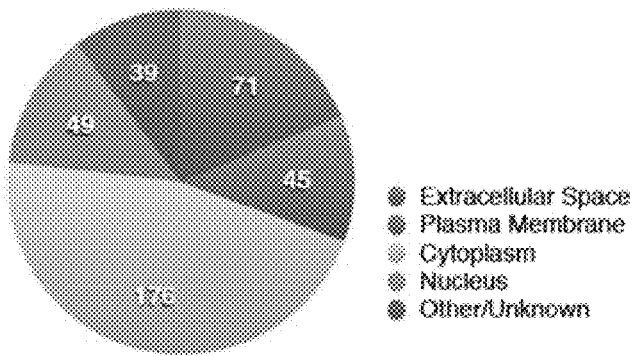
Figure 4:
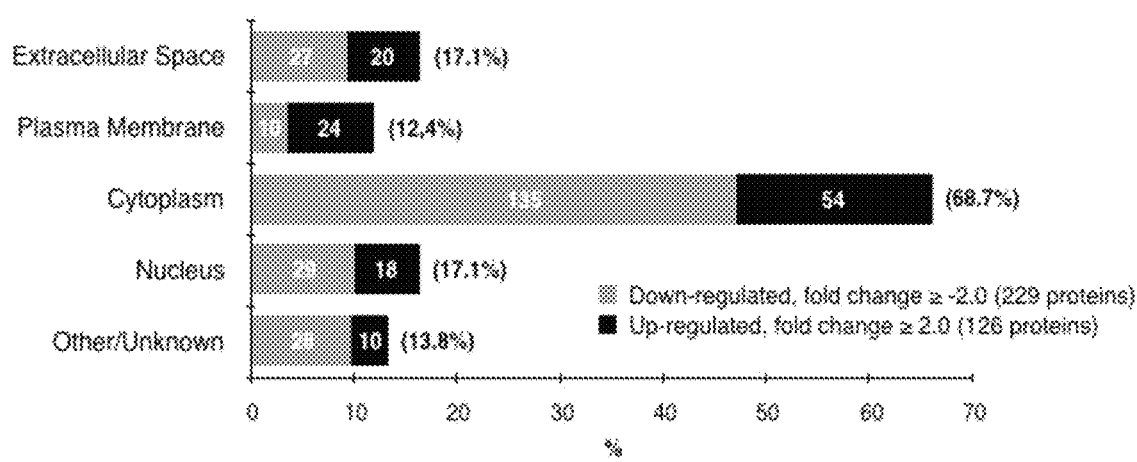
FIG. 4 summarizes the classification of the subcellular localization of 355 differentially expressed proteins in the urothelium of OAB rats and their expression status (up-regulated or down regulated) compared to normal urothelium.

Cellular component analysis was performed to find the subcellular localization of the identified proteins. Of the 507 proteins identified in the sham rat urothelium, 84 (16.6%) proteins were extracellular proteins, 39 (7.7%) proteins were located in the plasma membrane, and 259 (51.1%) proteins were located in the cytoplasm, and 66 (13.0%) proteins were found in the nucleus (FIG. 3A). Proteins identified in the OAB rat urothelium also exhibited similar protein localization. 71 (18.7%) proteins were extracellular proteins, 45 (11.8%) proteins were located on the plasma membrane, and 176 (46.3%) proteins were located in the cytoplasm and 49 (12.9) proteins were found in nuclei (FIG. 3B). When comparing the intracellular location of differentially expressed proteins, it was generally believed that the protein in the subcellular region was inhibited while the membrane protein was newly synthesized or overexpressed in OAB urothelium (FIG. 4). In conclusion, proteomic analysis showed that the total number of proteins expressed in the urothelium of the bladder is reduced in OAB model animals (FIG. 2), but the number of plasma membrane proteins expressed in urothelium is increased (FIG. 4). As shown in FIG. 4, of the 24 up-regulated (i.e., increased expression) plasma membrane proteins, three transfer factors (Anxa5, Slc12a7, Vamp8), two ion channels (Cacna2d1, P2rx1) and two receptors (Lgals3 bp, Pgrmc1) were identified. This suggests that OAB urothelium can detect, accept, or release chemical stimuli. The OAB is much more sensitive than normal bladder. Thus, these upregulated urothelial plasma membrane proteins may be the cause of OAB, and targeting these proteins can become a new therapeutic strategy.

TABLE 2

| Flod Change (OAB/normal) | No. of proteins |
|---|---|
| OAB only | 74 |
| Fold change ≥ 2 | 52 |
| 2 > Fold change > 0 | 137 |

TABLE 2-continued

| Flod Change (OAB/normal) | No. of proteins |
|---|---|
| 0 > Fold change > −2 | 89 |
| Fold change ≤−2 | 28 |
| Normal only | 201 |
| Total | 581 |

Example 3: Functional Annotation of Differentially Expressed Proteins

Figure 5:
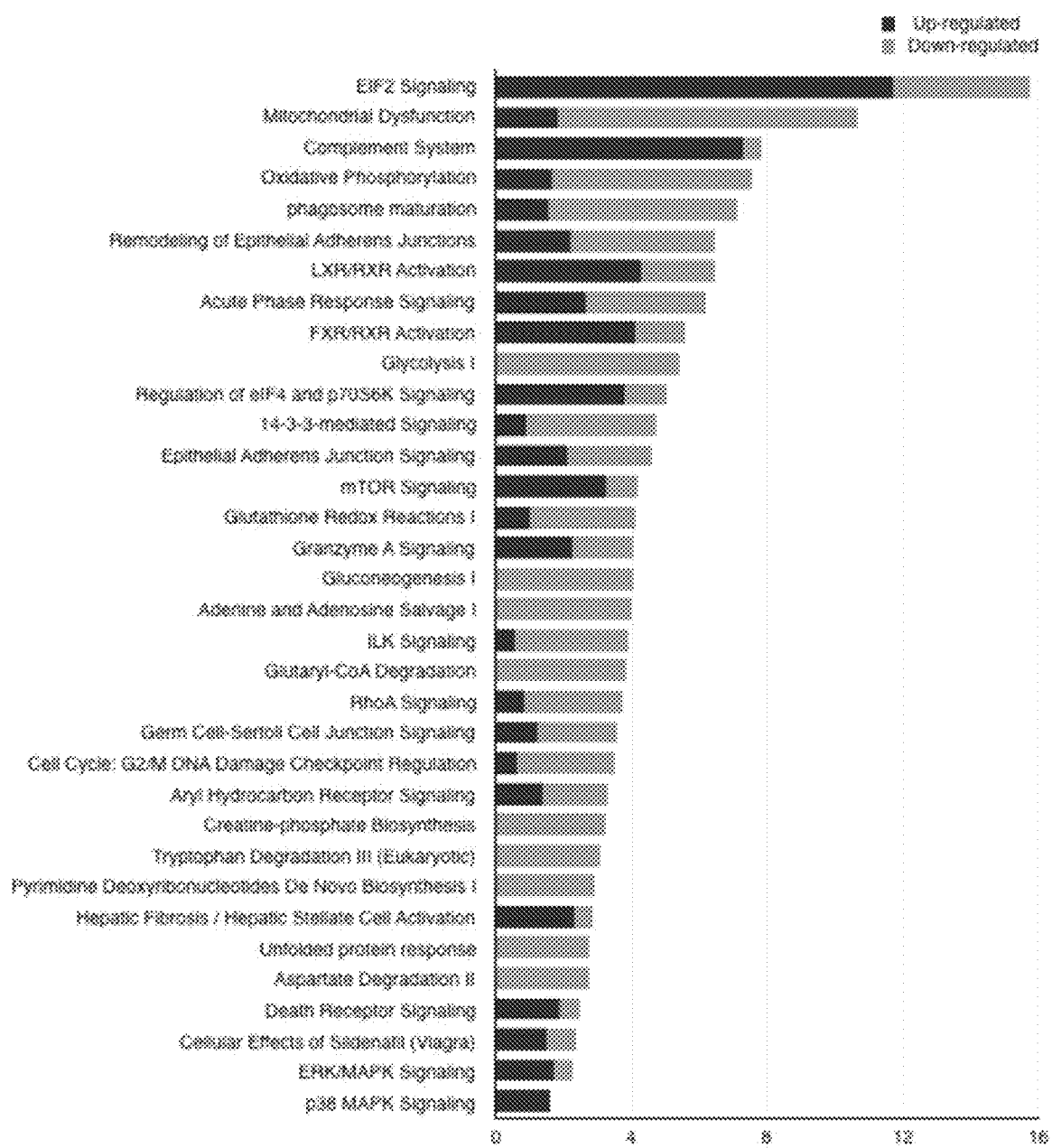
FIG. 5 shows the results of the functional annotation of 355 differentially expressed proteins in the urothelium of OAB rats compared to normal urothelium using the IPA tool. A total of 34 normal pathways including the top 20 normal pathways in the normal and OAB rat urothelium were showed. For each path, we indicate whether the up-regulation pattern is large or down-regulation pattern in the OAB state.

In order to analyze the data at the pathway and network level, 355 differentially expressed proteins were analyzed using Ingenuity Pathway Analysis (IPA). The 34 identified canonical pathways are shown in FIG. 5, which represents the top 20 most significant canonical pathways combined in the urothelium of sham control and OAB. In OAB urothelium, inflammatory pathways such as the complement system, acute phase response signaling, LXR/RXR activation and p38 MAPK signaling have been markedly up-regulated. In contrast, signaling pathways associated with cytoskeletal organization including ILK signaling, RhoA signaling, and remodeling of epithelial adherence junctions are generally down-regulated in OAB urothelium. Proteins involved in unfolded protein response (ER stress) were down-regulated and proteins involved in death receptor signaling were up-regulated.

Example 4: Analysis of Upstream Regulator of QAB

The above-described proteomic analysis showed significant differences in the protein expression and the signal pathways involved between the normal (sham control) urothelium and OAB urothelium. Bioinformatic analysis was performed using IPA to investigate potential causes of OAB. As a result of the analysis, 17 putative upstream regulators were identified for proteins identified as differentially expressed in OAB in the previous examples (Table 3). These regulators were mainly involved in inflammation and cytoskeleton formation. CR1L (complement component 3b/4b receptor 1-like), HTT (huntingtin) and INHA (inhibin α) acted as upstream regulators of Cryab, Aldoa, Tpm2, My19, Cnn1, Myh11 and C3. In addition, the six upstream regulator, HTT (huntingtin), INHA (inhibin α), ITGA2 (integrin a2), CR1L (complement component 3b/4b receptor 1-like), HNF1B (HNF1 homeobox B), and PDGF (platelet-derived growth factor family), which regulate the inflammatory response were identified, and these can affect cell migration of leukocytes and neutrophils as well as cellular infiltration of leukocytes through the regulation of many other proteins identified in urothelium. As shown in Table 3 below, additional functional studies of upstream signaling factors and their downstream effectors (differential expressions of OAB were described in the above Examples) can provide molecular evidence for the cause of abnormal physiological phenomena in detrusor in OAB.

TABLE 3

Protein network analysis of OAB upstream regulator

| Network | Upstream Regulators | Diseases & Functions | Identified Target Molecules |
|---|---|---|---|
| 1 | CR1L(complement component 3b/4b receptor 1-like), | Cell movement of leukocytes, | ALDOA, APOA1, BGN, C3, CD9, CNN1, COL18A1, COL1A1, COL4A1, CRYAB, |

TABLE 3-continued

Protein network analysis of OAB upstream regulator

| Network | Upstream Regulators | Diseases & Functions | Identified Target Molecules |
|---|---|---|---|
|  | HTT(huntingtin), INHA(inhibin alpha), ITGA2(integrin subunit alpha 2) | Formation of epithelial tissue, Muscle contraction | DCN, FN1, GSN, HSPD1, ITGA5, ITGB1, LUM, MCAM, MYH11, MYL9, PFN1, SERPINA1, SERPINA3, SERPINE1, SERPINF1, Tpm2, YBX1 |
| 2 | CR1L(complement component 3b/4b receptor 1-like), SMAD7(SMAD family member 7) | Advanced stage solid tumor, Metastatic solid tumor | COL18A1, COL4A1, COL6A3, FN1, NID2, SERPINE1 |
| 3 | HNF1B(HNF1 homeobox B), HTT(huntingtin), ITGA2(integrin subunit alpha 2), PDGF(family, platelet derived growth factor) | Cellular infiltration by leukocytes | APOA1, BGN, CRYAB, DCN, FGB, FN1, HSPD1, ITGB1, MCAM, SERPINA1, SPARC, YBX1 |
| 4 | APP(amyloid beta precursor protein), NFE2L2(nuclear factor erythroid 2 like 2) | Cell movement of sarcoma cell lines | CTSB, FN1, SERPINE1, SERPINF1, SOD2, STMN1, VCP |
| 5 | ANGPT2(angiopoietin 2), GH1(growth hormone 1), Phenylbutazone, Prednisolone | Anemia | ANXA1, APOE, C3, C4A/C4B, CFB, CP, CRP, FN1, HBB, LGALS3, PRDX1, PRDX2, PRDX3, RPS6, SOD1, SOD2, TF |
| 6 | miR-122-5p (miRNAs w/seed GGAGUGU) | Carcinoma in lung, Cell viability of tumor cell lines | ALDOA, GPX7, P4HB, PKM, PRDX2, VIM |
| 7 | HNF1B(HNF1 homeobox B) | Cell movement of neutrophils, Cellular infiltration by leukocytes | ALB, BGN, FGB, FN1, LUM, SERPINA1, SPARC |
| 8 | ANGPT2(angiopoietin 2), Tanespimycin | Endoplasmic reticulum stress response | CALR, DNAJB4, HSP90AB1, HSPA5, HSPD1, SERPINH1, SOD1 |
| 9 | INSR(insulin receptor) ITGAV(integrin subunit alpha V) | Proliferation of muscle cells | CTSB, FHL1, FN1, HSPD1, ITGA5, OGN, SERPINE1, VTN |
| 10 | Phenylbutazone | Anemia Hemostasis | ANXA1, ANXA2, C4A/C4B, CP, FGB, LGALS3 |

Example 5: Proteins Involved in Signal Transduction in the Bladder Urothelium The urothelium secretes a number of signaling molecules to communicate with adjacent interstitial cells such as the bladder nerve, detrusor smooth muscle (DSM) and myofibroblast. Typical signal molecules secreted from urothelium are adenosine triphosphate (ATP), nitric oxide (NO), prostaglandin (PG), protachykinin-1 (TAC1), Ach and nerve growth factor (NGF).

Figure 6:
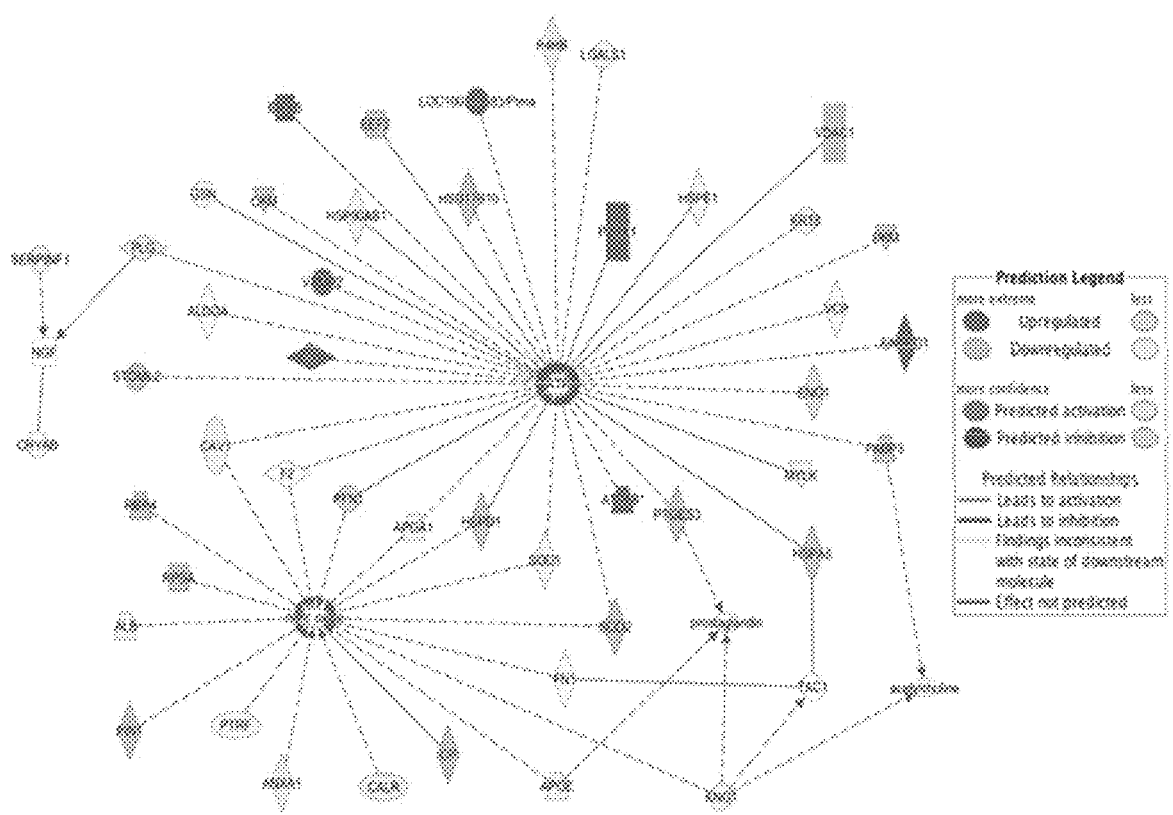
FIG. 6 shows network analysis results for signal molecules secreted from the urothelium and their control proteins identified in the present invention (Red: upregulated, green: downregulated). The networks of proteins involved in signaling molecules secreted from the urothelium such as ATP, NO, PG, TAC1, Ach, and NGF were identified using the IPA method.
Figure 7A:
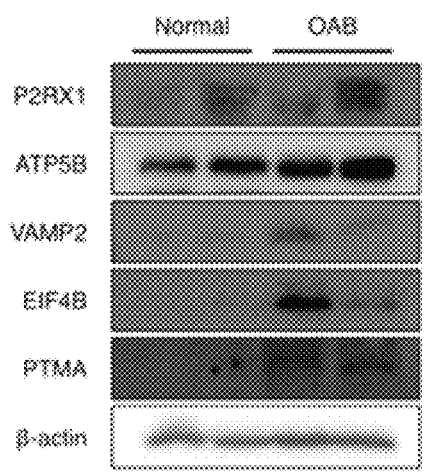
FIG. 7A shows the result of Western blotting that the P2RX1, ATP5B, VAMP2, EIF4B and PTMA proteins were up-regulated only in the OAB urothelium.
Figure 7B:
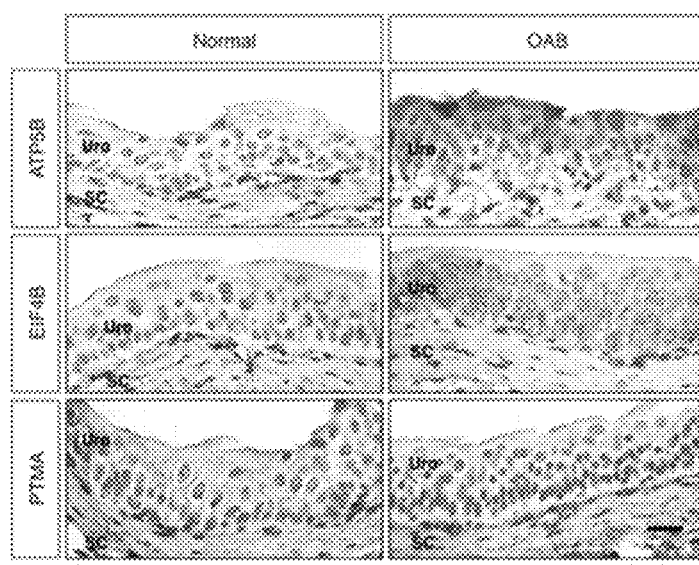
FIG. 7B shows the results of immunohistochemistry that the ATP5B, EIF4B and PTMA proteins were up-regulated only in the OAB urothelium (Uro: urothelium layer, SC: suburothelial connective tissue layer, the scale bar indicates 50 µm (bottom)).

In order to confirm the novel regulatory factors of the signal molecules in the urothelium, the protein network analysis of the proteins, which have been confirmed to be differentially expressed in the OAB rat urothelium in the above-mentioned example, was performed. As a result, 52 proteins capable of regulating the signal molecules in urothelium were identified (FIG. 6). Among the identified proteins, 34 proteins can regulate the production or release of ATP, and 18 proteins can regulate the production and release of NO (FIG. 6). Of the 34 ATP-related proteins, only 7 proteins (ENTPD1, P2RX1, ATP5B, VAMP2, C3, EIF4B and PTMA) showed a specific detection tendency only in the urothelium of OAB. Specifically, ENTPD1, VAMP2, C3, EIF4B, and PTMA were detected only in OAB compared to sham, and expression levels in P2RX1 and ATP5B were significantly increased in OAB. This expression pattern was verified by Western blot and immunohistochemistry (FIG. 7). On the other hand, seven of the 18 NO-related proteins (RBP4, RPSA, PIN2, CP, SOD2, HSPD1 and PEF1) were expressed only in the normal bladder urothelium and completely blocked in the OAB urothelium. In the above example, the factors selected as the regulatory factors are differentially expressed in the OAB. Thus, not only do they have very important significance as markers in themselves, but they also provide a therapeutic strategy for OAB by adjusting their levels to normal levels.

Example 6: Potential Diagnostic Markers in QAB

Figure 8:
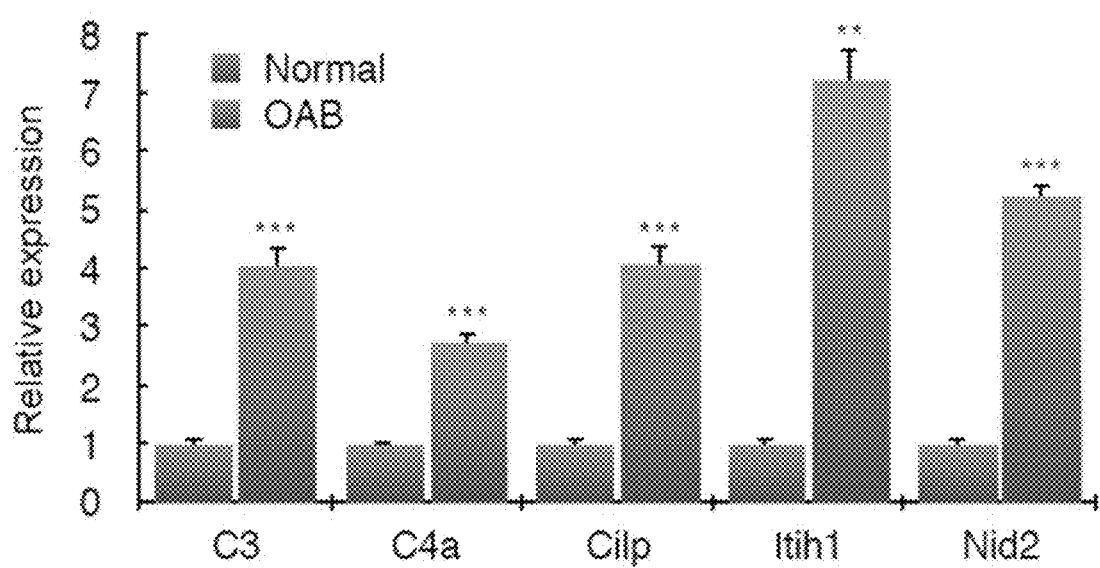
FIG. 8 shows the results of q-RT PCR confirmed that C3, C4a, Clip, Itih1, and Nid2 genes were up-regulated only in the OAB urinary tract epithelium (The data are presented as relative expression following normalization. Data represented mean±SD.  $p<0.005$, * $p<0.001$ versus normal).

Because there is no known molecular diagnostic marker for OAB, the clinical diagnosis of OAB is still symptom-based. As described above, in this study, the protein expression in urothelium was dynamically changed by OAB. Thus, the proteins that display different expression patterns in OAB urothelium can be used as potential diagnostic markers for OAB. Urothelium is an outermost barrier tissue that is in direct contact with the urine. Extracellular proteins expressed by urothelium, which are released into the urine, can also be used as noninvasive OAB diagnostic markers. 37 extracellular proteins exclusively expressed were identified in normal (sham control) or OAB rat urothelium (Table 4). Of these, eleven proteins were expressed only in urothelium of OAB. The remaining 24 proteins were expressed only in normal urothelium (Table 4). These potential marker proteins are closely related to pathophysiological changes in OAB. In addition, real-time PCR experiments confirmed that expression levels of up-regulated proteins in OAB such as C3, C4a, Clip, ITIH1, and NID2 were increased (FIG. 8). Detection of these proteins or their peptide fragments in the urine is considered to be useful for the diagnosis of OAB. By selecting the agents which change (especially, normalize) them by using their expression (and activity), it is possible to screen drugs for the prevention or treatment of OAB disease which is more accurate and more effective.

TABLE 4

Potential diagnostic markers in OAB

| Symbol | Gene Name |
|---|---|
| | Up-regulated |
| C2 | complement component 2 |
| C3 | complement component 3 |
| C4B | complement component 4B (Chido blood group) |
| C4A | complement component 4A |
| CFH | complement factor H |
| CILP | cartilage intermediate layer protein, nucleotide pyrophosphohydrolase |
| IGFBP7 | insulin-like growth factor binding protein 7 |
| ITIH1 | inter-alpha-trypsin inhibitor heavy chain 1 |
| MGP | matrixGla protein |
| NID2 | nidogen 2 (osteonidogen) |
| PF4 | platelet factor 4 |
| | Down-regulated |
| 1300017J02Rik | 1300017J02Rik protein (RIKEN cDNA 1300017J02 gene cording protein) |
| A1BG | alpha-1-B glycoprotein |
| CFL2 | cofilin 2 (muscle) |
| CP | ceruloplasmin (ferroxidase) |
| CPA3 | carboxypeptidase A3 (mast cell) |
| ECM1 | extracellular matrix protein 1 |
| FBLN5 | fibulin 5 |
| FGB | fibrinogen beta chain |
| FMOD | fibromodulin |
| GPX3 | glutathione peroxidase 3 (plasma) |
| HBA1 | hemoglobin alpha 1 |
| HBA2 | hemoglobin alpha 2 |
| HP | haptoglobin |
| ITIH4 | inter-alpha-trypsin inhibitor heavy chain family, member 4 |
| LAMC1 | laminin, gamma 1 (formerly LAMB2) |
| LTBP4 | latent transforming growth factor beta binding protein 4 |
| PCOLCE | procollagen C-endopeptidase enhancer |
| PRG2 | proteoglycan 2, bone marrow (natural killer cell activator, eosinophil granule major basic protein) |
| PXDN | peroxidasin |
| RBP4 | retinol binding protein 4, plasma |
| SERPINA6 | serpin peptidase inhibitor, clade A (alpha-1 antiproteinase, antitrypsin), member 6 |
| SUSD2 | sushi domain containing 2 |
| TINAGL1 | tubulointerstitial nephritis antigen-like 1 |
| TNC | tenascin C |

As described above, the present invention relates to a biomarker for diagnosis of overactive bladder (OAB) disease, and a method for screening a drug using the biomarker. The markers described in the present invention can effectively detect or diagnose the onset of OAB by distinguishing them from normal populations. In particular, OAB-specific protein markers released into urine enable simple and rapid OAB diagnosis in a non-invasive manner, and it offers considerable advantages in the application of diagnostic kits and is therefore highly industrially applicable. In addition, by selecting an agent that changes (particularly normalizes) the expression (and activity) of the markers selected in the present invention, more effective agent for the prevention or treatment of OAB disease can be screened. Such an agent can be highly applicable in the pharmaceutical industry.

What is claimed is:

1. A method for diagnosing and treating overactive bladder disease in a subject, the method comprising:
    (a) obtaining a biological sample from a suspected subject of overactive bladder disease,
    (b) measuring the expression level of EIF4B(Eukaryotic translation initiation factor 4B) in the biological sample;
    (c) diagnosing the subject with overactive bladder disease when the expression or detection level of EIF4B from the biological sample is greater than that of a normal control sample; and
    (d) treating the diagnosed subject by administering an effective amount of a therapeutic agent for overactive bladder disease.

2. The method of claim 1, wherein step (b) is conducted by an agent comprising
    (I) an antibody which specifically binds to EIF4B(Eukaryotic translation initiation factor 4B), a peptide or aptamer having a binding domain specific to EIF4B (Eukaryotic translation initiation factor 4B); or
    (II) a primer or a probe which specifically binds to mRNA of a gene encoding EIF4B(Eukaryotic translation initiation factor 4B).

3. The method of claim 2, wherein the probe is an oligonucleotide probe, a single stranded DNA probe, a double stranded DNA probe or a RNA probe.

4. The method of claim 1, wherein step (b) is conducted by a kit comprising an agent for measuring the expression level of EIF4B(Eukaryotic translation initiation factor 4B) in the biological sample.

5. The method of claim 1, wherein the method further comprises:
    in step (b) measuring or detecting the expression level of Anxa5(Annexin A5), Slc12a7(solute carrier family 12 member 7), Vamp8(Vesicle-associated membrane protein 8), Cacna2d1(Voltage-dependent calcium channel subunit alpha-2/delta-1), Lgals3 bp(galectin 3 binding protein), Pgrmcl(Membrane-associated progesterone receptor component 1), ENTPD1(Ectonucleoside Triphosphate Diphosphohydrolase 1), P2RX1(P2X purinoceptor 1), ATP5B(ATP synthase subunit beta), VAMP2(Vesicle-associated membrane protein 2), PTMA(Prothymosin Alpha), C2(complement component 2), C3(complement component 3), C4A(complement component 4A), C4B(complement component 4B), CFH(complement factor H), CILP(cartilage intermediate layer protein), IGFBP7(insulin-like growth factor binding protein 7), ITIH1(inter-alpha-trypsin inhibitor heavy chain 1), MGP(matrixGla protein), NID2(nidogen 2), PF4(platelet factor 4), RBP4(Retinol binding protein 4), RPSA(40S ribosomal protein SA), PIN2(Auxin efflux carrier component 2), CP(ceruloplasmin), SOD2(superoxide dismutase 2), HSPD1(60 kDa heat shock protein family D member 1), PEF1 (Peflin), 1300017J02Rik protein, AlBG(alpha-l-B glycoprotein), CFL2(cofilin 2), CPA3(carboxypeptidase A3), ECM1(extracellular matrix protein 1), FBLN5 (fibulin 5), FGB(fibrinogen beta chain), FMOD(fibromodulin), GPX3(glutathione peroxidase 3), HBA1(hemoglobin alpha 1), HBA2(hemoglobin alpha 2), HP(haptoglobin), ITIH4(inter-alpha-trypsin inhibitor heavy chain family member 4), LAMC1(laminin gamma 1), LTBP4(latent transforming growth factor beta binding protein 4), PCOLCE(procollagen C-endopeptidase enhancer), PRG2(proteoglycan 2), PXDN (peroxidasin), SERPINA6(serpin peptidase inhibitor Glade A member 6), SUSD2(sushi domain containing 2), TINAGL1(tubulointerstitial nephritis antigen-like 1) or TNC(tenascin C) in the biological sample; and in step (c) diagnosing the subject with overactive bladder disease when (i) the expression or detection level of EIF4B from the biological sample is greater than that of a normal control sample, and the expression or detection level of Anxa5, Slc12a7, Vamp8, Cacna2d1, Lgals3 bp, Pgrmcl, ENTPD1, P2RX1, ATPSB, VAMP2, PTMA, C2, C3, C4A, C4B, CFH, CILP, IGFBP7, ITIH1, MGP, NID2 or PF4 from the biological sample is greater than that of a normal control sample, or (ii) the expression or detection level of EIF4B from the biological sample is greater than that of a normal control sample, and the expression or detection level of RBP4, RPSA, PIN2, CP, SOD2, HSPD1, PEF1, 1300017J02Rik protein, A1BG, CFL2, CPA3, ECM1, FBLNS, FGB, FMOD, GPX3, HBA1, HBA2, HP, ITIH4, LAMC1, LTBP4, PCOLCE, PRG2, PXDN, SERPINA6, SUSD2, TINAGL1 or TNC from the biological sample is smaller than that of a normal control sample.

6. The method of claim 5, wherein measuring or detecting of the expression levels of step (b) is conducted by use of an agent comprising
 (I) an antibody which specifically binds to a listed protein of step (b), a peptide or aptamer having a binding domain specific to a listed protein of step (b); or
 (II) a primer or a probe which specifically binds to mRNA of a gene encoding a listed protein of step (b).

\* \* \* \* \*